(12) United States Patent
Wiles et al.

(10) Patent No.: US 11,341,648 B2
(45) Date of Patent: *May 24, 2022

(54) COLONY CONTRAST GATHERING

(71) Applicant: BD KIESTRA B.V., Drachten (NL)

(72) Inventors: Timothy M. Wiles, Manchester, MD (US); Raphael Rodolphe Marcelpoil, Corenc (FR)

(73) Assignee: Timothy M. Wiles, Drachten (NL)

( * ) Notice: Subject to any disclaimer, the term of this patent is extended or adjusted under 35 U.S.C. 154(b) by 61 days.

This patent is subject to a terminal disclaimer.

(21) Appl. No.: 16/875,082

(22) Filed: May 15, 2020

(65) Prior Publication Data
US 2020/0342604 A1 Oct. 29, 2020

Related U.S. Application Data

(63) Continuation of application No. 16/681,333, filed on Nov. 12, 2019, now Pat. No. 10,692,216, which is a
(Continued)

(51) Int. Cl.
*G06T 7/11* (2017.01)
*G06T 7/00* (2017.01)
(Continued)

(52) U.S. Cl.
CPC .......... *G06T 7/0016* (2013.01); *C12M 23/10* (2013.01); *C12M 23/22* (2013.01); *C12M 25/06* (2013.01);
(Continued)

(58) Field of Classification Search
CPC . G06T 7/0016; G06T 7/11; G06T 7/13; G06T 7/90; G06T 3/0068; G06T 7/60;
(Continued)

(56) References Cited

U.S. PATENT DOCUMENTS 4,700,298 A 10/1987 Palcic
4,724,215 A 2/1988 Farber et al.
(Continued)

FOREIGN PATENT DOCUMENTS

CN 1582327 A 2/2005
CN 103518224 A 1/2014
(Continued)

OTHER PUBLICATIONS

International Search Report from International Application PCT/US2016/028913 dated Dec. 9, 2016.
(Continued)

*Primary Examiner* — Ali Bayat
(74) *Attorney, Agent, or Firm* — Botos Churchill IP Law LLP

(57) ABSTRACT

An imaging system and method for microbial growth detection, counting or identification. One colony may be contrasted in an image that is not optimal for another type of colony. The system and method provides contrast from all available material through space (spatial differences), time (differences appearing over time for a given capture condition) and color space transformation using image input information over time to assess whether microbial growth has occurred for a given sample.

5 Claims, 21 Drawing Sheets

Related U.S. Application Data continuation of application No. 15/567,775, filed as application No. PCT/US2016/028913 on Apr. 22, 2016, now Pat. No. 10,521,910.

(60) Provisional application No. 62/318,483, filed on Apr. 5, 2016, provisional application No. 62/151,681, filed on Apr. 23, 2015.

(51) Int. Cl.

| | |
|---|---|
| *C12M 1/00* | (2006.01) |
| *C12M 1/34* | (2006.01) |
| *C12M 1/36* | (2006.01) |
| *C12M 1/22* | (2006.01) |
| *G06V 10/40* | (2022.01) |
| *G06V 20/69* | (2022.01) |
| *G06T 7/13* | (2017.01) |
| *G06T 7/90* | (2017.01) |
| *C12M 1/12* | (2006.01) |
| *C12Q 1/02* | (2006.01) |
| *G01N 21/27* | (2006.01) |
| *G01N 33/569* | (2006.01) |
| *G06K 9/62* | (2022.01) |
| *G06T 3/00* | (2006.01) |
| *G06T 7/60* | (2017.01) |

(52) U.S. Cl.
CPC ............ *C12M 31/02* (2013.01); *C12M 41/14* (2013.01); *C12M 41/46* (2013.01); *C12M 41/48* (2013.01); *C12Q 1/02* (2013.01); *G01N 21/27* (2013.01); *G01N 33/56911* (2013.01); *G06K 9/6256* (2013.01); *G06T 3/0068* (2013.01); *G06T 7/11* (2017.01); *G06T 7/13* (2017.01); *G06T 7/60* (2013.01); *G06T 7/90* (2017.01); *G06V 10/40* (2022.01); *G06V 20/69* (2022.01); *G06V 20/693* (2022.01); *G06V 20/695* (2022.01); *G06V 20/698* (2022.01); *G06T 2207/10024* (2013.01); *G06T 2207/10056* (2013.01); *G06T 2207/10152* (2013.01); *G06T 2207/30024* (2013.01)

(58) Field of Classification Search
CPC . G06T 2207/30024; G06T 2207/10024; G06T 2207/10056; G06T 2207/10152; G06T 7/30; G06K 9/00127; G06K 9/00134; G06K 9/0014; G06K 9/00147; G06K 9/6256; G06K 9/46; C12M 23/10; C12M 25/06; C12M 31/02; C12M 23/22; C12M 41/14; C12M 41/46; C12M 41/48; C12Q 1/02; G01N 21/27; G01N 33/56911
USPC ......................................................... 382/106
See application file for complete search history.

(56) References Cited

U.S. PATENT DOCUMENTS

| | | | |
|---|---|---|---|
| 5,403,722 A | 4/1995 | Floeder et al. | |
| 5,694,478 A * | 12/1997 | Braier | C12Q 1/04 382/133 |
| 5,723,308 A | 3/1998 | Mach et al. | |
| 5,976,892 A | 11/1999 | Bisconte | |
| 6,122,396 A | 9/2000 | King et al. | |
| 6,385,272 B1 | 5/2002 | Takahashi | |
| 6,605,446 B2 | 8/2003 | Eden | |
| 6,718,077 B1 | 4/2004 | Cruz-Fiocruz | |
| 7,106,889 B1 | 9/2006 | Mahers et al. | |
| 7,298,886 B2 | 11/2007 | Plumb et al. | |
| 7,319,031 B2 | 1/2008 | Vent et al. | |
| 7,351,574 B2 | 4/2008 | Vent | |
| 7,496,225 B2 | 2/2009 | Graessle et al. | |
| 7,582,415 B2 | 9/2009 | Straus | |
| 7,666,355 B2 | 2/2010 | Alavie | |
| 7,738,689 B2 | 6/2010 | Plumb et al. | |
| 7,865,008 B2 | 1/2011 | Graessle et al. | |
| 7,957,575 B2 | 6/2011 | Plumb et al. | |
| 8,134,177 B2 | 3/2012 | Murooka | |
| 8,260,026 B2 | 9/2012 | Plumb et al. | |
| 8,417,013 B2 | 4/2013 | Bolea et al. | |
| 8,570,370 B2 | 10/2013 | McCollum et al. | |
| 8,588,505 B2 | 11/2013 | Bolea | |
| 8,759,080 B2 | 6/2014 | Graessle et al. | |
| 8,831,326 B2 | 9/2014 | Nishida et al. | |
| 8,840,840 B2 | 9/2014 | Bolea | |
| 8,855,397 B2 | 10/2014 | Moy et al. | |
| 8,895,255 B1 | 11/2014 | Goldberg et al. | |
| 8,896,706 B2 | 11/2014 | van den Hengel et al. | |
| 9,012,209 B2 | 4/2015 | Eden et al. | |
| 9,042,967 B2 | 5/2015 | Dacosta et al. | |
| 9,292,729 B2 | 3/2016 | Guthrie et al. | |
| 9,359,631 B2 | 6/2016 | Dupoy et al. | |
| 9,378,545 B2 | 6/2016 | Bise et al. | |
| 9,400,242 B2 | 7/2016 | Allano et al. | |
| 9,470,624 B2 | 10/2016 | Guthrie et al. | |
| 9,567,621 B2 | 2/2017 | Robinson et al. | |
| 9,576,181 B2 | 2/2017 | Allano et al. | |
| 9,606,046 B2 | 3/2017 | Decaux et al. | |
| 2003/0082516 A1 | 5/2003 | Straus | |
| 2003/0227612 A1 | 12/2003 | Fein et al. | |
| 2004/0253660 A1 | 12/2004 | Gibbs et al. | |
| 2005/0213845 A1 | 9/2005 | Avinash et al. | |
| 2006/0009912 A1 * | 1/2006 | Thijsen | G16B 20/20 702/19 |
| 2007/0177149 A1 | 8/2007 | Aronkyto | |
| 2009/0035808 A1 * | 2/2009 | Zoch | C12N 1/20 435/39 |
| 2011/0105623 A1 * | 5/2011 | Benjamin | A61K 9/0014 514/711 |
| 2011/0211058 A1 | 9/2011 | McCollum et al. | |
| 2012/0225449 A1 * | 9/2012 | Roth | C12Q 1/04 435/34 |
| 2014/0056504 A1 | 2/2014 | Lee et al. | |
| 2014/0219553 A1 | 8/2014 | Van Den Hengel | |
| 2014/0278136 A1 | 9/2014 | Shamsheyeva et al. | |
| 2015/0225684 A1 | 8/2015 | Spicer et al. | |
| 2015/0268163 A1 | 9/2015 | Dupoy et al. | |
| 2015/0299639 A1 | 10/2015 | Kleefstra et al. | |
| 2015/0339513 A1 | 11/2015 | Bolea | |
| 2015/0353983 A1 | 12/2015 | Drazek et al. | |
| 2016/0040215 A1 * | 2/2016 | Henn | C12Q 1/689 506/2 |
| 2016/0060676 A1 | 3/2016 | Lei | |
| 2016/0083686 A1 | 3/2016 | Triva | |
| 2016/0093033 A1 | 3/2016 | Allano et al. | |
| 2016/0098840 A1 | 4/2016 | Allano et al. | |
| 2016/0328844 A1 | 11/2016 | Triva | |
| 2018/0094291 A1 * | 4/2018 | Bjork | C12M 23/04 |

FOREIGN PATENT DOCUMENTS

| | | |
|---|---|---|
| EP | 2578693 A1 | 4/2013 |
| EP | 1163362 B1 | 7/2013 |
| EP | 2430461 B1 | 3/2014 |
| EP | 2287284 B1 | 12/2016 |
| JP | H09187270 A | 7/1997 |
| JP | H10510706 A | 10/1998 |
| JP | 2015073452 A | 4/2015 |
| WO | 9618720 A1 | 6/1996 |
| WO | 03022999 A2 | 3/2003 |
| WO | 2010143420 A1 | 12/2010 |
| WO | 2012119191 A1 | 9/2012 |
| WO | 2013049440 A1 | 4/2013 |
| WO | 2014098994 A1 | 6/2014 |
| WO | 2014099643 A1 | 6/2014 |
| WO | 2015114121 A1 | 8/2015 |
| WO | 2015162364 A1 | 10/2015 |
| WO | 2015173490 A1 | 11/2015 |
| WO | 2016001555 A1 | 1/2016 |

(56) References Cited

FOREIGN PATENT DOCUMENTS

| WO | 2016011534 A1 | 1/2016 |
|---|---|---|
| WO | 2016083744 A1 | 6/2016 |
| WO | 2016097092 A1 | 6/2016 |
| WO | 2016172388 A2 | 10/2016 |
| WO | 2017006055 A1 | 1/2017 |

OTHER PUBLICATIONS

Anonymous , "Microbiology Online, Society for General Microbiology, Teachers—Observing Microbes—Observing Bacteria in a Petri Dish", Mar. 10, 2015, (Mar. 10, 2015).

Chatburn, L. T., et al., ""VAPI: low cost, Rapid Automated Visual Inspection System for Petri Plate Analysis"", Proc of SPIE, vol. 6755, (2007), pp. 1-11.

Chayadevi, M. L., et al., ""Data Mining, Classification and Clustering with Morphological Features of Microbes",", International Journal of Computer Applications, pp. 1-5, Aug. 1, 2012, (Aug. 1, 2012).

Chen, Wei-Bang , et al., ""An Automated Bacterial Colony Counting and Classification System",", Information Systems Frontiers, A Journal of Research and Innovation, Kluwer Academic Publishers, BO, vol. 11, No. 4, Feb. 18, 2009, (Feb. 18, 2009), pp. 349-368.

Otero, A., et al., ""Rapid Microbiological Methods in Meat and Meat Products", Meat Science Elsevier Science, GB,", vol. 49, Jan. 1, 1998, (Jan. 1, 1998), pp. S179-S189.

Sousa, Ana Margarida, et al., "Improvement on Colony Morphology Identification Towards Bacterial Profiling,", Journal of Microbiological Methods, vol. 95, No. 3, Jan. 1, 2013, (Jan. 1, 2013), pp. 327-335.

Souvenir, Richard , et al., ""Cell Motion Analysis Without Explicit Tracking"", Computer Vision and Pattern Recognition, 2008. CVPR 2008, IEEE Conference on IEEE, Piscataway NJ, USA, Jun. 23, 2008, (Jun. 23, 2008), pp. 1-7.

First Office Action issued in Chinese application No. 2016800229997 dated Aug. 14, 2020.

Extended Search Report issued in European application No. 20195493.0 dated Oct. 30, 2020.

First Examination Report issued in Indian application No. 201717041116 dated Jun. 22, 2021, 10 pp.

Japanese Office Action issued in corresponding JP application No. 2020-168832 dated Sep. 9, 2021, 8 pp.

Office Action dated Jul. 7, 2020 received in corresponding Japanese Application No. 2018-506804, pp. 4. (Machine generated translation).

Office Action dated Jun. 16, 2020 received in corresponding Brazilian Application No. BR112017022830-0, pp. 4.

\* cited by examiner

400

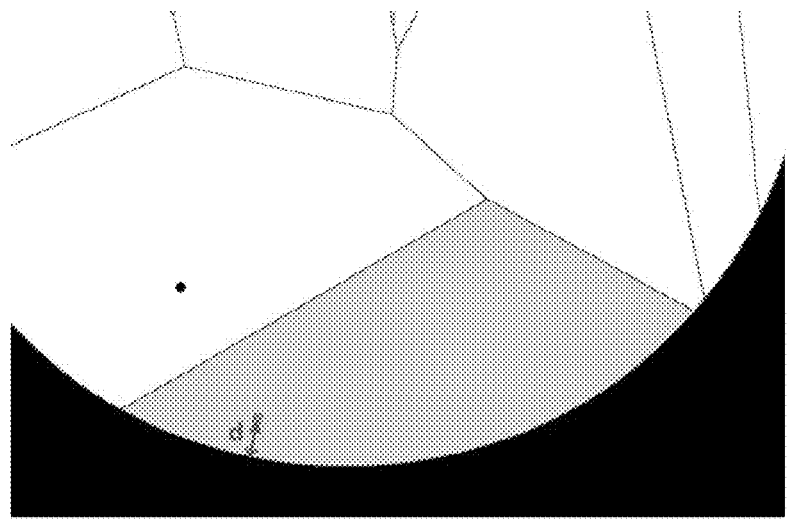
FIGURE 13A
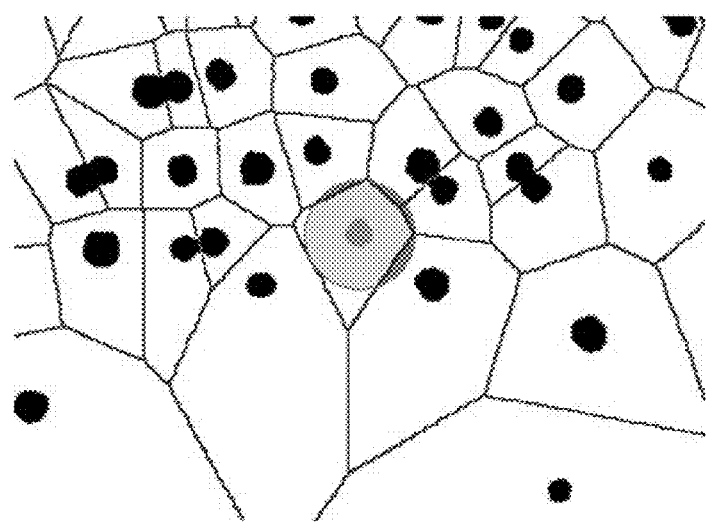
FIGURE 13B
FIGURE 13C
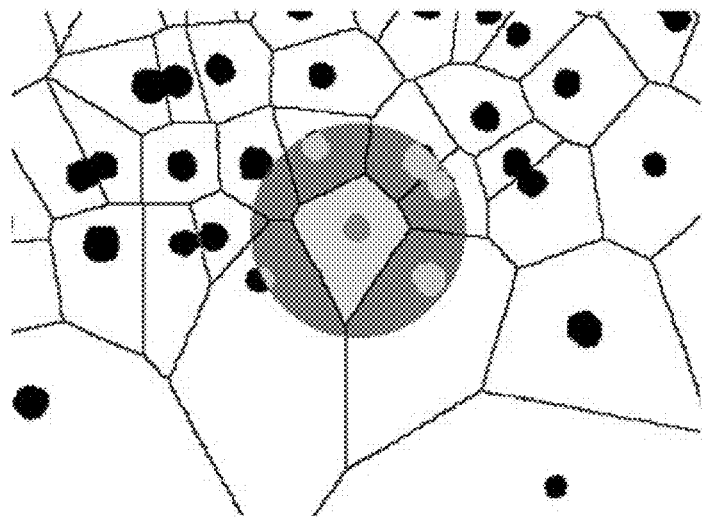

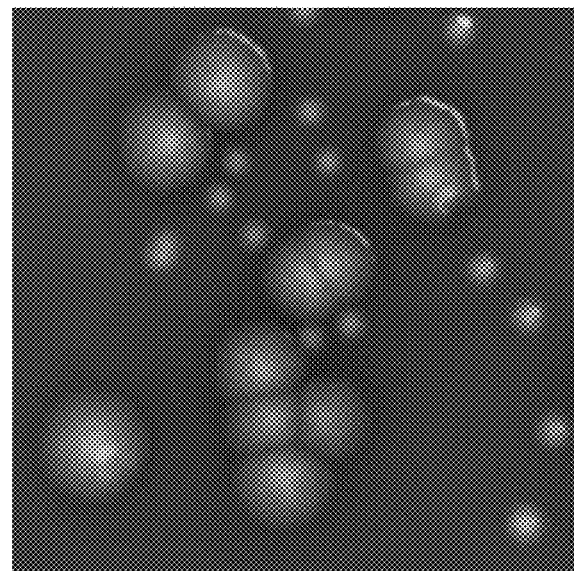
FIGURE 15A
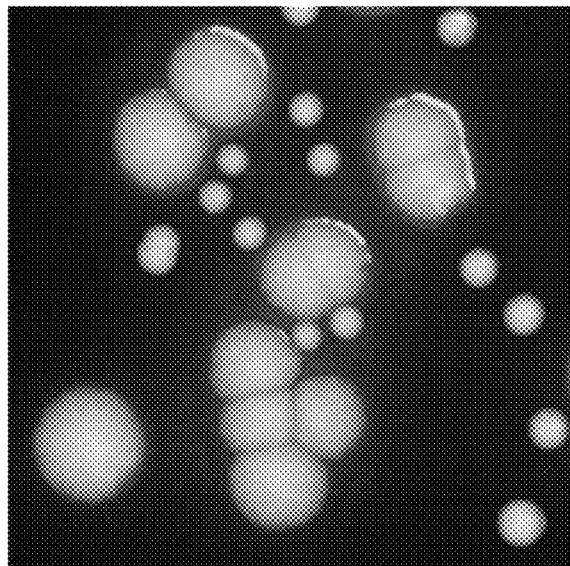
FIGURE 15B
FIGURE 15C
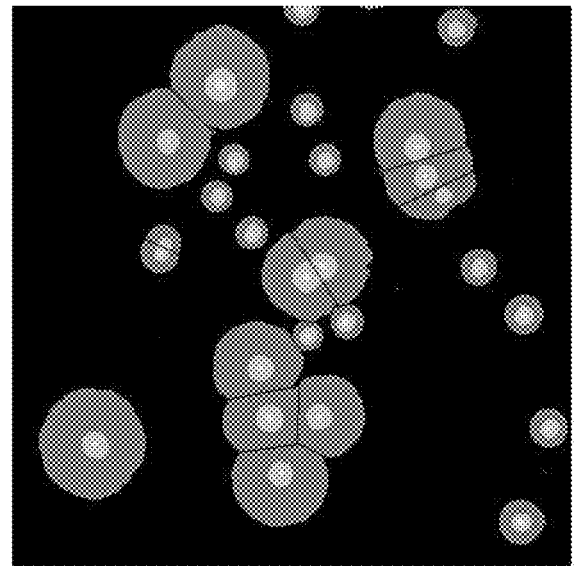

COLONY CONTRAST GATHERING

CROSS-REFERENCE TO RELATED APPLICATIONS

The present application is a continuation of U.S. application Ser. No. 16/681,333 filed Nov. 12, 2019, which is allowed, which application is a continuation of U.S. application Ser. No. 15/567,775 filed Oct. 19, 2017, now U.S. Pat. No. 10,521,910, issued Dec. 31, 2019 and is a national phase entry under 35 U.S.C. § 371 of International Application No. PCT/US2016/028913 filed Apr. 22, 2016 published in English, which claims priority from U.S. Provisional Application No. 62/151,681, filed Apr. 23, 2015, and U.S. Provisional Application No. 62/318,483, filed Apr. 5, 2016, all of which are incorporated herein by reference.

BACKGROUND OF THE INVENTION

There is increased focus on digital imagery of culture plates for detection of microbial growth. Techniques for imaging plates for detecting microbial growth are described in PCT Publication No. WO2015/114121, the entirety of which is incorporated by reference herein. Using such techniques, laboratory staff is no longer required to read plates by direct visual inspection but can use high quality digital images for plate inspection. Shifting laboratory workflow and decision-making to examination of digital images of culture plates can also improve efficiency. Images can be marked by an operator for further work-up by either the operator or another person with the appropriate skills. Additional images may also be taken and used to guide secondary processes.

Detection of colonies, colony enumeration, colony population differentiation and colony identification define the objectives for a modern microbiology imaging system. Having these objectives realized as early as possible achieves the goals of delivering results to a patient quickly and providing such results and analysis economically. Automating laboratory workflow and decision-making can improve the speed and cost at which these goals may be achieved.

Although significant progress has been made regarding imaging technologies for detecting evidence of microbial growth, it is still sought to extend such imaging technologies to support an automated workflow. Apparatus and methods for inspecting culture plates for indications of microbial growth are difficult to automate, due in part to the highly visual nature of plate inspection. In this regard, it is desirable to develop techniques that may automatically interpret culture plate images and determine the next steps to be performed (e.g., identification of colonies, susceptibility testing, etc.) based on the automated interpretation.

For example, identifying and distinguishing colonies in a plated culture can be difficult, especially when the colonies are of different size and shape and are touching each other. These problems are exacerbated when growth has already reached confluence in some regions of the plate. For these reasons, it is preferable, if possible, to identify colonies and determine growth early in the process. However, time for incubation is still needed to allow for at least some growth of the colonies. Thus, on the one hand, the longer that colonies are allowed to grow, the more they begin to contrast with their background and each other, and the easier it becomes to identify them. Yet, on the other hand, if the colonies are allowed to grow too long and they begin to fill the plate and/or touch one another, it becomes more difficult to contrast them from their background and from one another. If one were able to detect colonies at an incubation time when the colonies were still small enough to be isolated from one another—despite relatively poor contrast—this problem could be minimized or even resolved.

BRIEF SUMMARY OF THE INVENTION

An aspect of the present disclosure is directed to an automated method for evaluating microbial growth on plated media, comprising: providing a culture media inoculated with a biological sample disposed in a container that is substantially optically transparent; incubating the inoculated culture media in an incubator; placing the transparent container carrying the inoculated culture media in the digital imaging apparatus; obtaining a first digital image of the inoculated culture media at a first time (to), the first digital image having a plurality of pixels; determining coordinates of the pixels in the first digital image relative to the container carrying the inoculated culture media; removing the container carrying the inoculated culture media from the digital imaging apparatus and placing the inoculated culture media in the incubator for further incubation; after further incubation, placing the container carrying the inoculated culture media in the digital imaging apparatus; obtaining a second digital image of the inoculated culture media at a second time (tx), the second digital image having a plurality of pixels; aligning the first digital image with the second digital image, such that the coordinates of a pixel in the second digital image correspond to the coordinates of a corresponding pixel in the first digital image; comparing the pixels of the second digital image with corresponding pixels of the first digital image; identifying pixels that changed between the first digital image and the second digital image, wherein the pixels that have not changed between the first digital image and the second digital image are indicative of background; determining which of the identified pixels in the second digital image have a predetermined level of threshold contrast with the pixels indicative of background; identifying one or more objects in the second digital image, each object consisting of pixels that meet said level of threshold contrast and that are not separated from each other by background pixels; for at least one of the identified objects, determining a morphology of the object from the pixels of the object; from the morphology of the object, determining whether the object is a colony candidate; and providing to memory the coordinates of the pixels associated with the object.

In some examples, the method may further comprise obtaining a plurality of first digital images at the first time according to a predetermined series of illumination conditions, wherein each of the first digital images is obtained under a different illumination condition, each illumination condition comprising a specified orientation of the optically transparent container carrying the inoculated culture media relative to an illumination source, and a specified background color on which the optically transparent container is placed in the image acquisition device. The specified orientations may comprise: the illumination source directed downward toward the top of the optically transparent container carrying the inoculated culture media; the illumination source directed upward toward the bottom of the optically transparent container carrying the inoculated culture media; and the illumination source directed toward a side of the optically transparent container carrying the inoculated culture media. For the specified top and side orientations, the specified background color may be black. For the specified bottom orientation, the specified background color may be white. The illumination conditions may further comprise a specified illumination spectrum comprising: an illumination source emitting red wavelengths; an illumination source emitting green wavelengths; and an illumination source emitting blue wavelengths.

In some examples, the method may further comprise obtaining object features from the pixel information associated with the object, the object features comprising at least one of object shape, object size, object edge and object color, wherein the morphology of the object is determined based on the object features. Object color may be determined from spectral features of the pixels associated with the object. Spectral features may be selected from the group consisting of pixel color, hue, luminance and chrominance. Background feature information may also be obtained. Background feature information may comprise media type and media color, and the morphology of the object may be determined based further on the background feature information. The object features and background feature information may be compared with other object features and other background feature information stored in the memory, and a type of microorganism may be determined based on the object features and background feature information.

In some examples, aligning the first digital image with the second digital image may comprise assigning polar coordinates to pixels of each of the first and second digital images such that the polar coordinates of a pixel in the second digital image are the same as the polar coordinates of a corresponding pixel in the first digital image. Also, in some examples, a plurality of culture media may be provided, inoculated with a biological sample, disposed in one or more optically transparent containers, incubated in an incubator, and placed in the image acquisition device at the same time frame of bacterial growth, whereby first and second digital images are obtained for each culture media. Also, in some examples, the method performed by the executed instructions may further comprise identifying pixel information in the first digital image that is evidence of condensation on the optically transparent container or plated media, and subtracting the pixel information attributed to condensation from the image. Pixel information that is evidence of condensation may be identified in a digital image for which the illumination source was directed upward toward the bottom of the optically transparent container, and wherein pixel information for those pixels having an optical density below a predetermined threshold value is subtracted from the image.

In some examples, the method may further comprise: identifying pixel information in either of the first and second digital images that is evidence of dust; and subtracting the pixel information attributed to dust from the image. Pixel information that is evidence of dust may be identified in a digital image for which: the optically transparent container contains white culture media, the illumination source is directed downward toward the top of the optically transparent container and the background color is black; the optically transparent container contains colored or dark culture media, the illumination source is directed downward toward the top of the optically transparent container and the background color is white; or the illumination source is directed upward toward the bottom of the optically transparent container. The dust may be dust on any of the culture media, on the optically transparent container, or an optical component of the image acquisition device.

In some examples, the method may further comprise: obtaining a third digital image of the inoculated media wherein the third digital image is obtained at a time between the time at which the first digital image is acquired and the time and which the second digital image is acquired, wherein the inoculated culture media is removed from the image acquisition device and placed in the incubator between the acquisition of the first and second digital images and between the acquisition of the second and third digital images; aligning the third digital image with the first digital image, such that the coordinates of a pixel in the third digital image are the same as the coordinates of a corresponding pixel in the first digital image; comparing the pixels of the third and second digital images with one another; and identifying pixels that changed between the third and second digital images. The incubation time between the first and third digital images may be equal to the incubation time between the third and second digital images. At least one of the identified objects may be associated with the identified pixels that changed between the third and second digital images.

In some examples, the method may further comprise: obtaining a third digital image of the inoculated media wherein the third digital image is obtained after the time at which the second digital image is obtained, wherein the inoculated culture media is removed from the image acquisition device and placed in the incubator between the time at which the second and third digital images are obtained; aligning the third digital image with the first and second digital images, such that the coordinates of a pixel in the third digital image are the same as the coordinates of a corresponding pixel in the first and second digital images; comparing the pixels of the third and second digital images with one another; identifying pixels that changed between the second and third digital images; and determining that an object identified in the second digital image has changed in the third digital image based on the compared pixels of the second and third digital images that were identified to have changed. An object identified in the second digital image that has been determined to change in the third digital image may be determined to be a seed object from which the extent of the determined change is evaluated. In such a case, the method performed by the executed instructions may further comprise updating the coordinates of the pixels associated with the object in the memory based on the pixels identified to have changed between the second and third digital images.

Another aspect of the present disclosure is directed to a method for identifying growth in a culture media inoculated with a biological sample and disposed in a substantially transparent container. The system comprises: an image acquisition device for capturing digital images of the culture media; memory storing information regarding candidate colony objects identified in the captured digital images; and one or more processors operable to execute instructions to perform a method. The method comprises: at the onset of incubation of the media ($t_0$), obtaining a first digital image of the media, the first digital image having a plurality of pixels; assigning coordinates to one or more pixels of the first digital image; after a period of incubation for the media ($t_x$), obtaining a second digital image of the media, the second digital image having a plurality of pixels; aligning the second digital image with the first digital image, wherein said alignment is based on the coordinates assigned to the pixels of the first image and one or more pixels of the second image corresponding to the pixels of the first image that were assigned the coordinates; generating spatial contrast data indicative of changes between locally adjacent pixels of the second digital image; generating temporal contrast data indicative of changes between corresponding pixels of the first and second digital images; for each of a plurality of pixels of the second digital image, assigning a contrast value to the pixel based on a combination of the spatial contrast data and the temporal contrast data of the pixel; associating adjacent pixels having contrast values that are greater than a predetermined threshold and within a predetermined margin of error of one another, the associated pixels constituting an identified object; and storing each identified object in the memory as a candidate colony.

In some examples, combining the spatial and temporal contrast data comprises averaging the spatial and temporal contrast data. The spatial and temporal contrast data may be combined according to a weighted average.

Generating spatial contrast data may comprise: obtaining a plurality of images at time $t_x$, each of the plurality of images being obtained under different illumination conditions; processing spatial data in each of the plurality of $t_0$ images; and combining the processed spatial data. Processing the spatial data may comprise separately processing spatial data results for each illumination condition, and selecting a maximum result from the separately processed spatial data results.

Generating temporal contrast data may comprise: obtaining a plurality of images at time $t_0$, each of the plurality of images being obtained under different illumination conditions; obtaining a plurality of images at time $t_x$, the illumination conditions of each image at time $t_x$ corresponding to the illumination conditions of an image obtained at time $t_0$; processing temporal data in each of the corresponding $t_0$ and $t_x$ images; and combining the processed temporal data. Processing the temporal data may comprise separately processing temporal data results for each illumination condition, and selecting a maximum result from the separately processed temporal data results.

In some examples, the method may further comprise, for a given identified object: obtaining a plurality of object features from the pixel information associated with the object, wherein the object features comprise at least one morphometric feature, the morphometric feature being at least one of an object shape, object area, object perimeter or object edge; combining the object features using a classification algorithm; comparing the combined object features to object feature information for a plurality of microorganisms stored in the memory; and classifying the identified object as a type of microorganism based on the comparison. The object features may further comprise at least one spectral feature, the spectral feature being at least one of an object color, object brightness, object hue, object chroma, or at least one temporal feature (the temporal feature being at least one of an object growth rate, a change in object color, or a projected time that the object was first visually observable). At least one of the object features may be obtained for each pixel of the identified object, and then combined using one or more statistical histogram features. The classification algorithm may be a supervised machine learning algorithm, wherein the combined object features may be compared to object feature information for four or fewer microorganisms stored in the memory.

In some examples, the method may further comprise, for a given identified object: for each pixel of the identified object, assigning a temporal contrast value to the pixel based on the temporal contrast data of the pixel; identifying one or more maxima from the assigned temporal contrast values; if more than one maximum is identified, determining whether the maxima are associated with a common colony forming unit or with different colony forming units; and for any two maxima determined to be associated with different colony forming units, segmenting the identified object into two objects based at least in part on the respective locations of said two maxima. Determining whether two maxima are associated with a common colony forming unit or with different colony forming units may further comprise: for each maximum, determining a distance from the maximum to an edge of the identified object; calculating an inclusion factor value based on each determined distance and the distance between the two maxima; and comparing the inclusion factor value to a predetermined range, wherein the maxima are associated with a common colony forming unit if the inclusion factor value is less than the predetermined range, and the maxima are associated with different colony forming units if the inclusion factor value is greater than the predetermined range. If the inclusion factor value is within the predetermined range, the method may yet further comprise: for each maximum, determining a region surrounding the maximum; and calculating a convexity of the respective regions surrounding the maxima, wherein if the convexity is greater than a threshold value, the maxima are associated with different colony forming units.

In some examples, the method may further comprise: identifying one or more objects in a digital image first in time based on the spatial contrast data; and, for a given identified object in a digital image second in time, if the combined spatial and temporal contrast data for the object in the digital image second in time matches the spatial contrast data for an object identified in the digital image first in time, classifying the object in the second digital image as an artifact.

Yet another aspect of the present disclosure is directed to a method for evaluating microbial growth on plated media that has been inoculated with a culture and incubated, the method comprising: obtaining first and second digital images of the plated media, each digital image obtained after a period of incubation for the inoculated media and at a different time; aligning the second digital image with the first digital image, wherein said alignment is based on the coordinates assigned to the pixels of the first image and one or more pixels of the second image corresponding to the pixels of the first image that were assigned the coordinates; generating temporal contrast data indicative of changes between corresponding pixels of the first and second digital images; identifying an object in the second digital image from the temporal contrast data; obtaining one or more dynamic object features of the identified object from the temporal contrast data; classifying the identified object as a type of organism based on the one or more dynamic object features; and storing the identified object and its classification in the memory. In some examples, the one or more dynamic object features may include a growth rate of the identified object, a change to a chromatic feature of the identified object, or a change in growth along an axis proximately normal to the plated media.

In some examples, the method may further comprise: obtaining a third digital image of the plated media after a period of incubation for the inoculated media and at a different time than the first and second digital images; aligning the third digital image with the first and second digital images; and generating temporal contrast data indicative of changes between corresponding pixels of the second and third digital images, wherein the object is identified based further on said temporal contrast data, and wherein the one or more dynamic object features of the identified object includes a second derivative of the temporal contrast data.

The one or more dynamic object features may include includes an object growth acceleration rate.

Yet a further aspect of the present disclosure is directed to computer-readable memory storage medium having program instructions encoded thereon configured to cause a processor to perform a method. The method may be any of the above methods for evaluating microbial growth on plated media, identifying microbial growth on plated media that has been inoculated with a culture and incubated, or evaluating microbial growth on plated media that has been inoculated with a culture and incubated.

An even further aspect of the present is directed to a system for evaluating growth in a culture media inoculated with a biological sample. The system comprises an image acquisition device for capturing digital images of the culture media, memory, and one or more processors operable to execute instructions to perform a method. In some examples, the memory may store information regarding the captured digital images, and the method performed by the executed instructions may be any one the above described methods for evaluating microbial growth on plated media. In other examples, the memory may store information regarding candidate colony objects identified in the captured digital images, and the method performed by the executed instructions may be any one the above described methods for identifying microbial growth on plated media that has been inoculated with a culture and incubated. In yet further examples, the memory may store information regarding one or more objects identified in the captured digital images, and one or more classifications of the identified objects, and the method performed by the executed instructions may be any one the above described methods for evaluating microbial growth on plated media that has been inoculated with a culture and incubated.

BRIEF DESCRIPTION OF THE DRAWINGS

FIGS. 13A, 13B and 13C are diagrams illustrating isolation factor measurements according to an aspect of the disclosure.

FIGS. 15A, 15B and 15C are images illustrating a characterization of colony growth according to an aspect of the disclosure.

DETAILED DESCRIPTION

The present disclosure provides apparatus, systems and methods for identifying and analyzing microbial growth in on plated media based in at least in part on contrast detected in one or more digital images of the plated media. Many of the methods described herein can be fully or partially automated, such as being integrated as part of a fully or partially automated laboratory workflow.

The systems described herein are capable of being implemented in optical systems for imaging microbiology samples for the identification of microbes and the detection of microbial growth of such microbes. There are many such commercially available systems, which are not described in detail herein. One example is the BD Kiestra™ ReadA Compact intelligent incubation and imaging system. Other example systems include those described in PCT Publication No. WO2015/114121 and U.S. Patent Publication 2015/0299639, the entirety of which is incorporated by reference herein. Such optical imaging platforms are well known to those skilled in the art and not described in detail herein.

Figure 1:
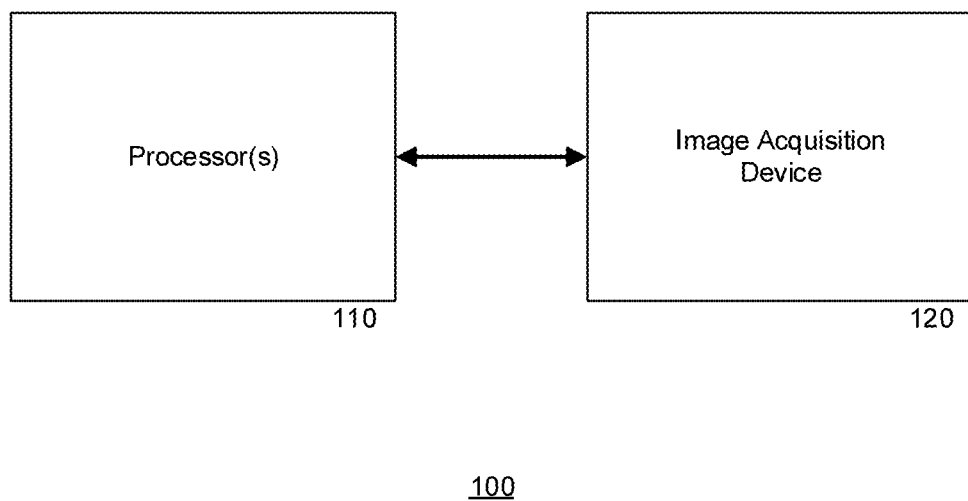
FIG. 1 is a schematic diagram of a system for imaging analyzing and testing a culture according to an aspect of the disclosure.

FIG. 1 is a schematic of a system 100 having a processing module 110 and image acquisition device 120 (e.g., camera) for providing high quality imaging of plated media. The processing module and image acquisition device may be further connected to, and thereby further interact with, other system components, such as an incubation module (not shown) for incubating the plated media to allow growth of a culture inoculated on the plated media. Such connection may be fully or partially automated using a track system that receives specimens for incubation and transports them to the incubator, and then between the incubator and image acquisition device.

The processing module 110 may instruct the other components of the system 100 to perform tasks based on the processing of various types of information. The processor 110 may be hardware that performs one or more operations. The processor 110 may be any standard processor, such as a central processing unit (CPU), or may be a dedicated processor, such as an application-specific integrated circuit (ASIC) or a field programmable gate array (FPGA). While one processor block is shown, the system 100 may also include multiple processors which may or may not operate in parallel, or other dedicated logic and memory for storing and tracking information related to the sample containers in the incubator and/or image acquisition device 120. In this regard, the processing unit may track and/or store several types of information regarding a specimen in the system 100, including but not limited to the location of the specimen in the system (incubator or image acquisition device, locations and/or orientation therein, etc.), the incubation time, pixel information of captured images, the type of sample, the type of culture media, precautionary handling information (e.g., hazardous specimens), etc. In this regard, the processor may be capable of fully or partially automating the various routines described herein. In one embodiment, instructions for performing the routines described herein may be stored on a non-transitory computer-readable medium (e.g. a software program).

Figure 2:
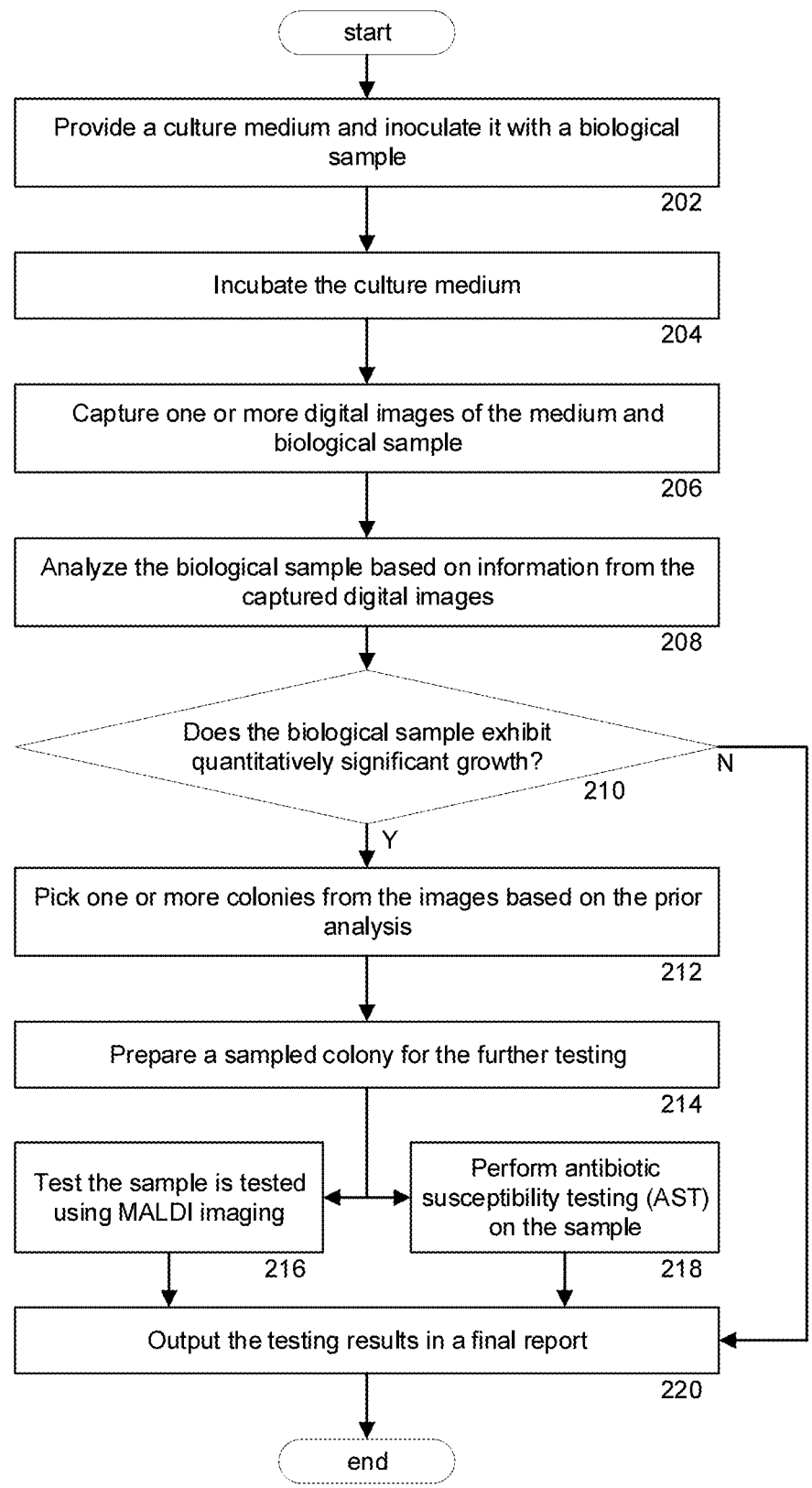
FIG. 2 is a flow chart illustrating an automated laboratory workflow routine for imaging analyzing and testing a culture according to an aspect of the disclosure.

FIG. 2 is a flow chart showing an example automated laboratory routine 200 for imaging, analyzing and, optionally, testing a culture. The routine 200 may be implemented by an automated microbiology laboratory system, such as the BD Kiestra™ Total Lab Automation or BD Kiestra™ Work Cell Automation. The example systems include interconnected modules, each module configured to execute one or more steps of the routine 200.

At 202, a culture medium is provided and inoculated with a biological sample. The culture medium may be an optically transparent container, such that the biological sample may be observed in the container while illuminated from various angles. Inoculation may follow a predetermined pattern. Streaking patterns and automated methods for streaking a sample onto a plate are well known to one skilled in the art and not discussed in detail herein. One automated method uses magnetically controlled beads to streak sample onto the plate. At 204, the medium is incubated to allow for growth of the biological sample.

At 206, one or more digital images of the medium and biological sample are captured. As will be described in greater detail below, digital imaging of the medium may be performed multiple times during the incubation process (e.g., at the start of incubation, at a time in the middle of incubation, at the end of incubation) so that changes in the medium may be observed and analyzed. Imaging of the medium may involve removing the medium from the incubator. Where multiple images are taken of the medium at different times, the medium may be returned to the incubator for further incubation between imaging sessions.

At 208, the biological sample is analyzed based on information from the captured digital images. Analysis of the digital image may involve analysis of pixel information contained in the image. In some instances, pixel information may be analyzed on a pixel by pixel basis. In other instances, pixel information may be analyzed on a block by block basis. In yet further instances, pixels may be analyzed based on entire regions of pixels, whereby the pixel information of individual pixels in the region may be derived by combining information of the individual pixels, selecting sample pixels, or by using other statistical methods such as the statistical histogram operations described in greater detail below. In the present disclosure, operations that are described as being applied to "pixels" are similarly applicable to blocks or other groupings of pixels, and the term "pixel" is hereby intended to include such applications.

The analysis may involve determining whether growth is detected in the medium. From an image analysis perspective, growth can be detected in an image by identifying an imaged object (based on differences between the object and its adjacent surroundings) and then identifying changes in the object over time. As described in greater detail herein, these differences and changes are both forms of "contrast." In addition to detecting growth, the image analysis at 108 may further involve quantifying the amount of growth detected, identifying distinct colonies, identifying sister colonies, etc.

At 210, it is determined whether the biological sample (particularly, the identified sister colonies) exhibits quantitatively significant growth. If no growth, or an insignificant amount of growth, is found, then the routine 200 may proceed to 220, in which a final report is output. In the case of proceeding from 210 to 220, the final report will likely indicate the lack of significant growth, or report the growth of normal flora.

If it is determined that the biological sample exhibits quantitatively significant growth, then at 212, one or more colonies may be picked from the images based on the prior analysis. Picking colonies may be a fully automated process, in which each of the picked colonies is sampled and tested. Alternatively, picking colonies may be a partially automated process, in which multiple candidate colonies are automatically identified and visually presented in a digital image to an operator, such that the operator may input a selection of one or more candidates for sampling and further testing. The sampling of selected or picked colonies may itself be automated by the system.

At 214, a sampled colony is prepared for the further testing, such as by plating the sample in an organism suspension. At 216, the sample is tested using matrix-assisted laser desorption ionization (MALDI) imaging to identify the type of specimen that was sampled from the original medium. At 218, the sample is also, or alternatively, subjected to antibiotic susceptibility testing (AST) to identify possible treatments for the identified specimen.

At 220, the testing results are output in a final report. The report may include the MALDI and AST results. As mentioned above, the report may also indicate a quantification of specimen growth. Thus, the automated system is capable of beginning with an inoculated culture medium and generating a final report regarding a specimen found in the culture, with little or no additional input.

In routines such as the example routine of FIG. 2, the detected and identified colonies are often referred to as Colony Forming Units (CFUs). CFUs are microscopic objects that begin as one or a few bacteria. Over time, the bacteria grow to form a colony. The earlier in time from when the bacteria are placed in the plate, the less bacteria there is to detect and, consequently the smaller the colony and the lower that contrast to the background. Stated another way, a smaller colony size yields a smaller signal, and a smaller signal on a constant background results in smaller contrast. This is reflected by the following equation:

$$\text{Contrast} = \frac{\text{Signal} - \text{background}}{\text{Signal} + \text{background}} \quad (1)$$

Contrast can play an important role in identifying objects, such as CFUs or other artifacts, in the images. An object can be detected in an image if it is significantly different in brightness, color and/or texture from its surroundings. Once an object has been detected, the analysis may also involve identifying the type of object that has been detected. Such identifications can also rely on contrast measurements, such as the smoothness of edges of the identified object, or the uniformity (or lack of uniformity) of the color and/or brightness of the object. This contrast must be great enough to overcome the image noise (background signals) in order to be detected by the image sensor.

The human perception of contrast (governed by Weber's law) is limited. Under optimal conditions, human eyes can detect a light level difference of 1%. The quality and confidence of image measurements (e.g., brightness, color, contrast) may be characterized by a signal-to-noise ratio (SNR) of the measurements, in which an SNR value of 100 (or 40 db), independent from pixel intensities, would match human detection capabilities. Digital imaging techniques utilizing high SNR imaging information and known SNR per pixel information can allow for detection of colonies even when those colonies are not yet visible to human eyes.

In the present disclosure, contrast may be collected in at least two ways: spatially and temporally. Spatial contrast, or local contrast, quantifies the difference in color or brightness between a given region (e.g., pixel, group of adjacent pixels) and its surroundings in a single image. Temporal contrast, or time contrast, quantifies the difference in color or brightness between a given region of one image against that same region in another image taken at a different time. The formula governing temporal contrast is similar to that for spatial contrast:

$$\text{Temporal Contrast} = \frac{|\text{Signal}(t_0) - \text{Signal}(t_1)|}{\text{Signal}(t_0) + \text{Signal}(t_1)} \quad (2)$$

In which $t_1$ is a time subsequent to $t_0$. Both spatial and temporal contrasts of a given image may be used to identify objects. The identified objects may then be further tested to determine their significance (e.g., whether they are CFUs, normal flora, dust, etc.).

Figure 3A:
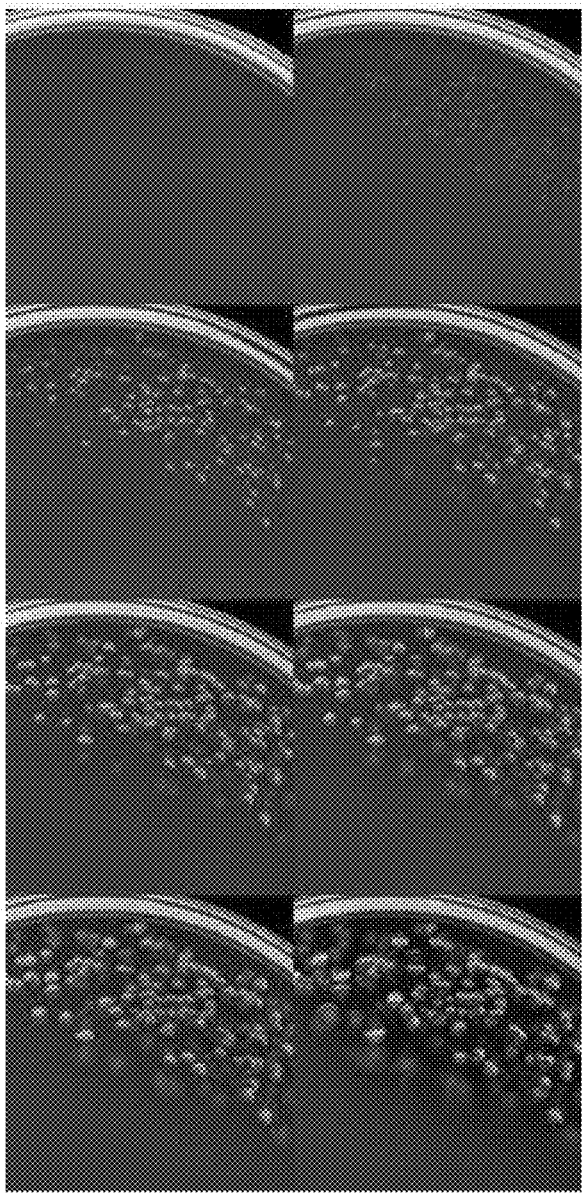
FIGS. 3A, 3B, and 3C are images showing a temporal contrast by a visual representation of colony morphology as it changes over time according to an aspect of the disclosure.
Figure 3B:
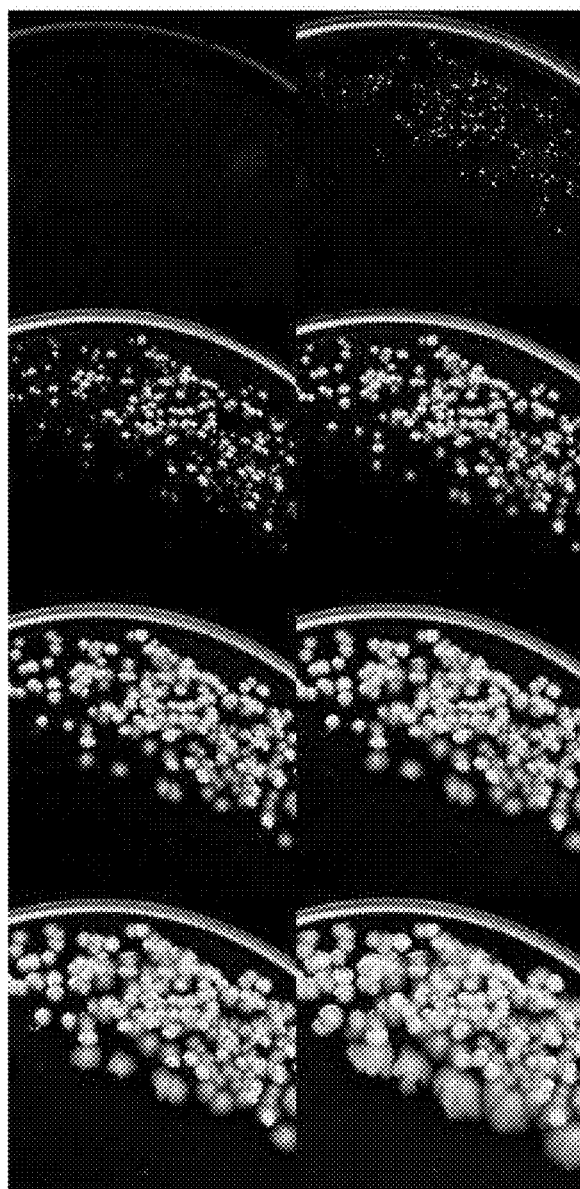
Figure 3C:
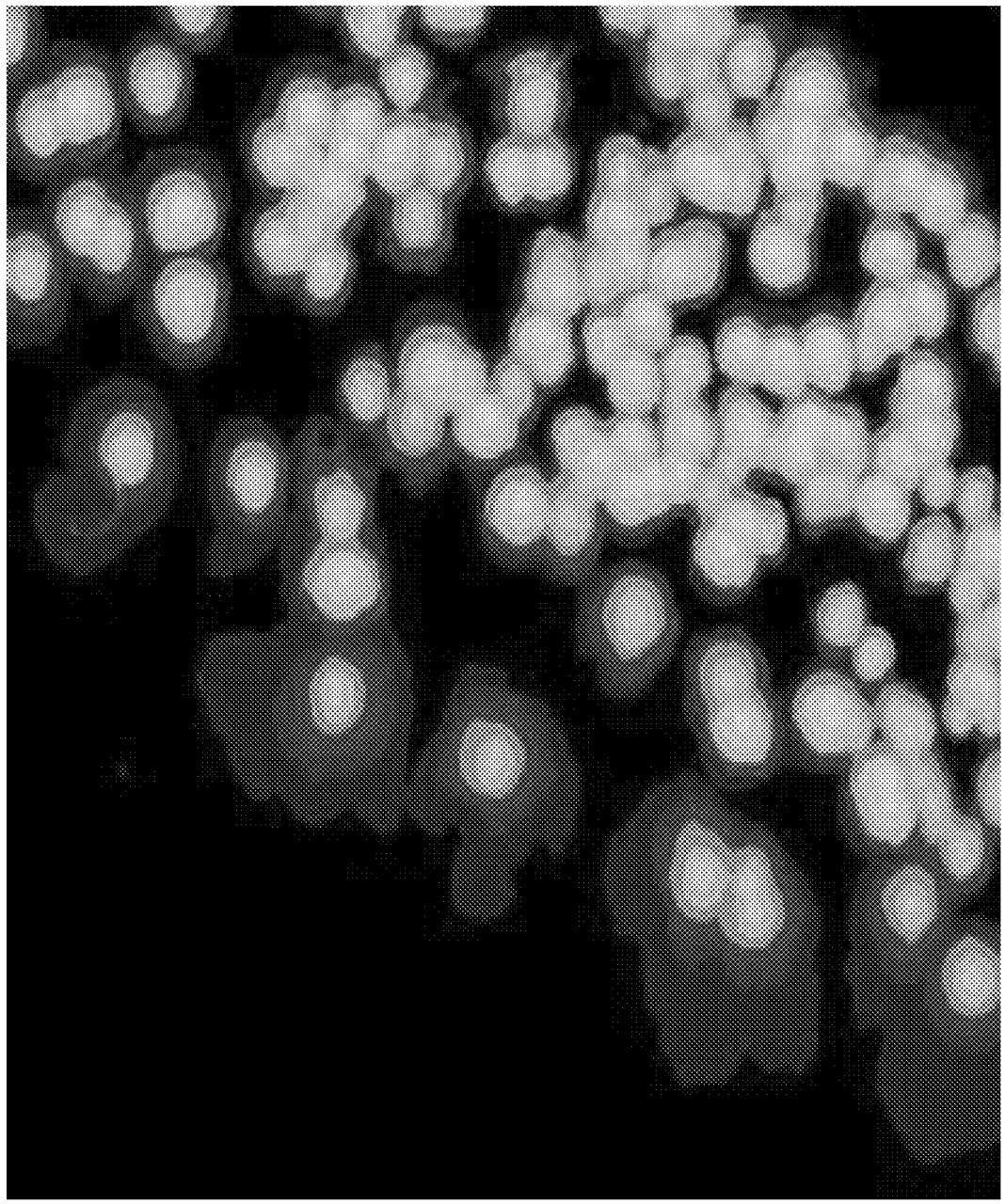

FIGS. 3A, 3B and 3C provide a visual demonstration of the effect that temporal contrast can have on an imaged sample. The images shown in FIG. 3A were captured at different points in time (left to right, top row to bottom row) showing the overall growth in the sample. While growth in noticeable in FIG. 3A, the growth is even more noticeable, and can be noticed even earlier in the sequence, from the corresponding contrast temporal images of FIG. 3B. For purposes of clarity, FIG. 3C shows a zoomed section of FIG. 3B. As can be seen in FIG. 3C, the longer a portion of a colony has been imaged, the brighter a spot it makes in the contrast image. In this way, the center of mass of each colony may be denoted by the bright center, or peak, of the colony. Thus, image data obtained over time can reveal important information about changes in colony morphology.

To maximize spatial or temporal contrast of an object against its background, the system may capture images using different incident lights on different backgrounds. For instance, any of top lighting, bottom lighting, or side lighting may be used on either a black or white background.

Figure 3D:
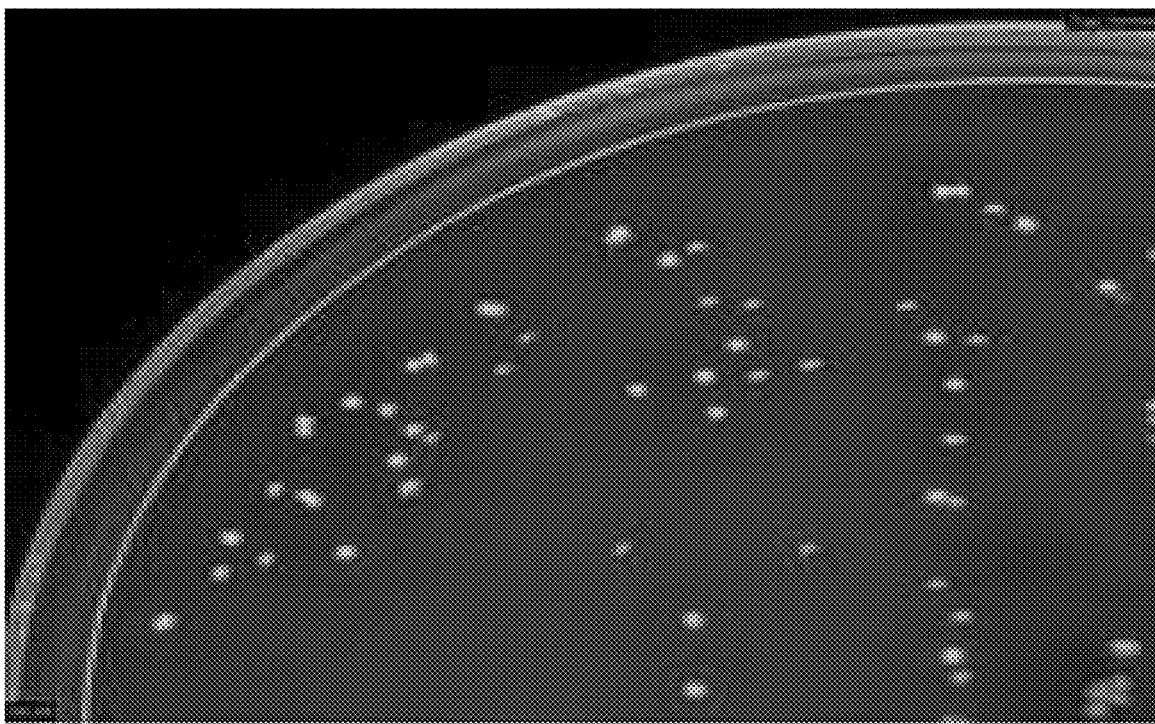
FIGS. 3D and 3E are images showing spatial contrast under different illumination conditions.
Figure 3E:
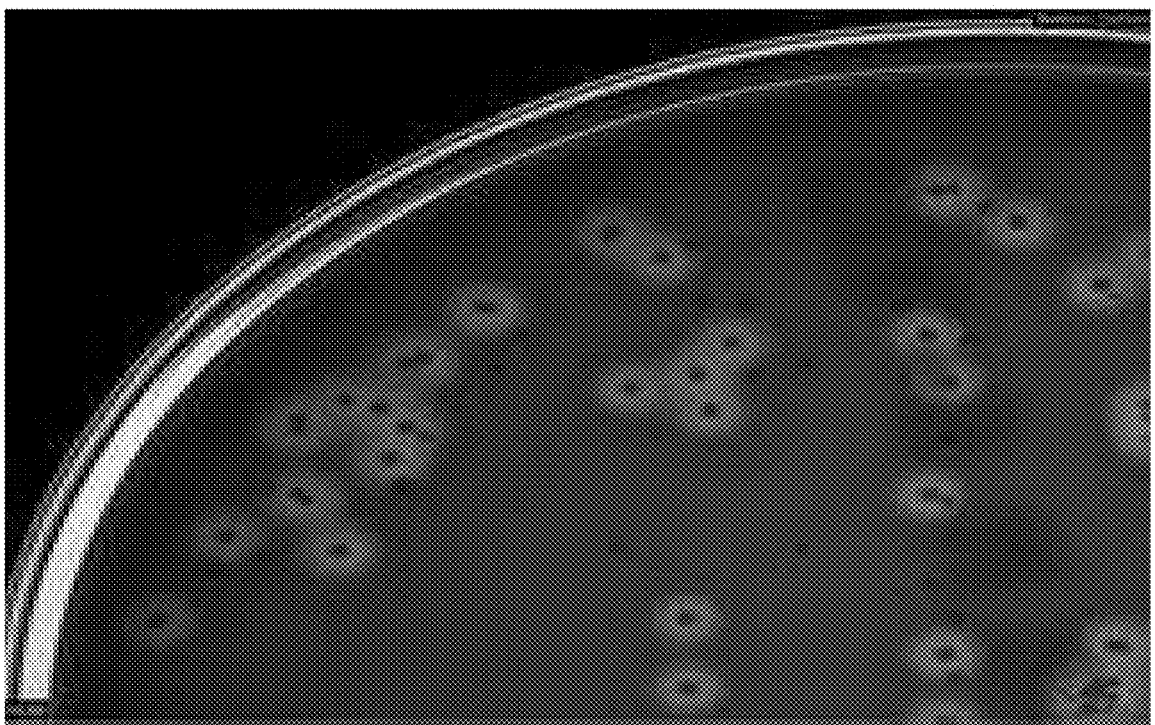

FIGS. 3D and 3E provide a visual demonstration of the effect that lighting conditions can have on an imaged sample. The image in FIG. 3D was captured using top lighting, whereas the image in FIG. 3E was captured at approximately the same time (e.g., close enough in time that no noticeable or significant growth has occurred) using bottom lighting. As can be seen, each of the images in the samples of FIGS. 3D and 3E contains several colonies, but additional information about the colonies (in this case, hemolysis) can be seen thanks to the back-lighting or bottom lighting in the image of FIG. 3D, whereas that same information is difficult to grasp in the image of FIG. 3E.

At a given point in time, multiple images may be captured under multiple illumination conditions. Images may be captured using different light sources that are spectrally different due to illumination light level, illumination angle, and/or filters deployed between the object and the sensor (e.g. red, green and blue filters). In this manner, the image acquisition conditions may be varied in terms of light source position (e.g., top, side, bottom), background (e.g., black, white, any color, any intensity), and light spectrum (e.g. red channel, green channel, blue channel). For instance, a first image may be captured using top illumination and a black background, a second image captured using side illumination and a black background, and a third image captured using bottom illumination and no background (i.e. a white background). Furthermore, specific algorithms may be used to create a set of varying image acquisition conditions in order to maximize spatial contrast using. These or other algorithms can also be useful to maximize temporal contrast by varying the image acquisition conditions according to a given sequence and/or over a span of time. Some such algorithms are described in PCT Publication No. WO2015/114121.

Figure 4:
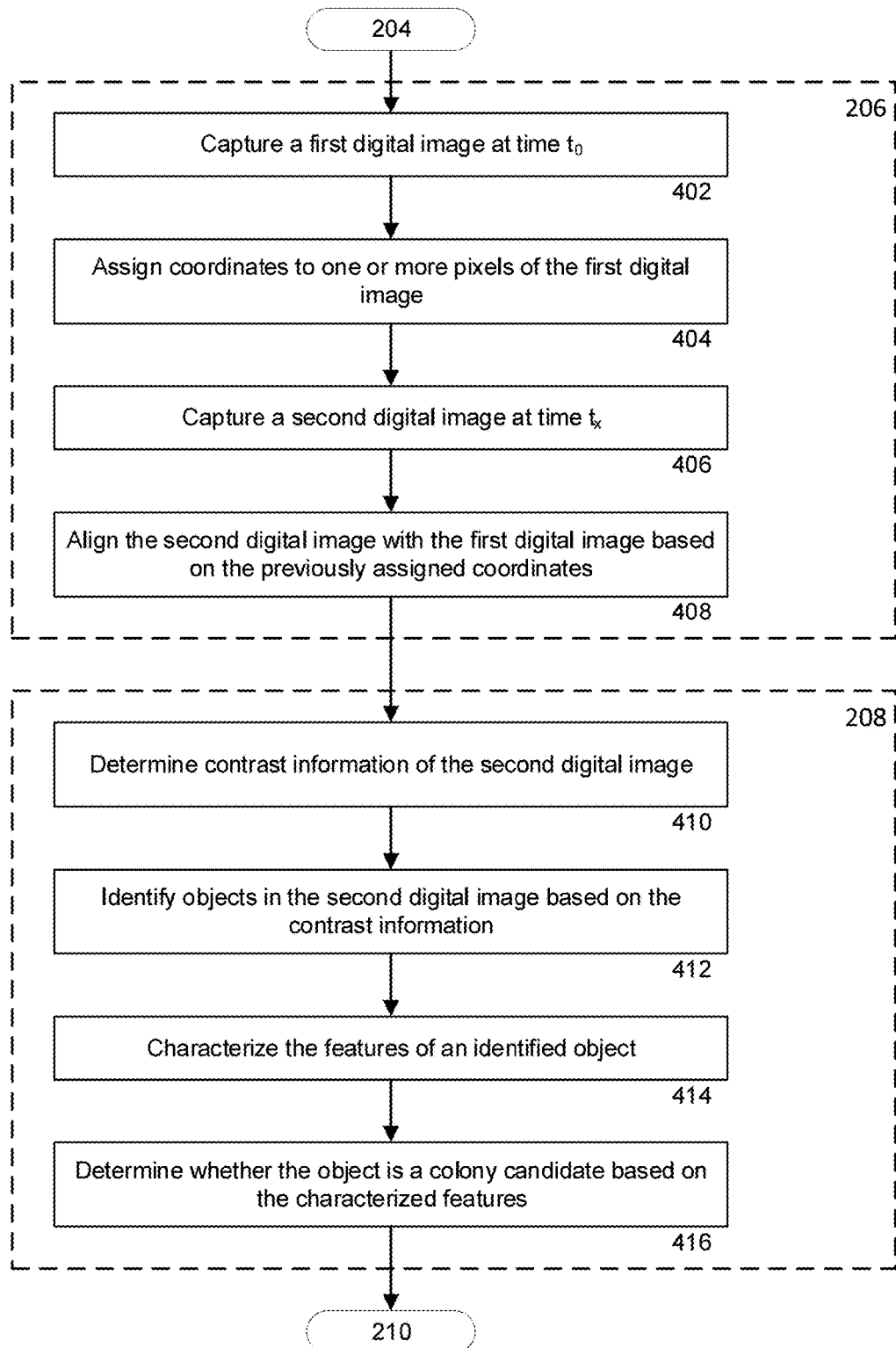
FIG. 4 is a flow chart of an example routine for obtaining and analyzing image information according to an aspect of the disclosure.

FIG. 4 is a flow chart showing an example routine for analyzing an imaged plate based at least in part on contrast. The routine of FIG. 4 may be thought of as an example subroutine of the routine 200 of FIG. 2, such that 206 and 208 of FIG. 2 are carried out at least in part using the routine of FIG. 4.

At 402, a first digital image is captured at time $t_0$. Time $t_0$ may be a time shortly after the incubation process has begun, such that bacteria in the imaged plate have not yet begun to form visible colonies.

At 404, coordinates are assigned to one or more pixels of the first digital image. In some instances, the coordinates may be polar coordinates, having a radial coordinate extending from a center point of the imaged plate and an angular coordinate around the center point. The coordinates may be used in later steps to help align the first digital image with other digital images of the plate taken from different angles and/or at different times. In some cases, the imaged plate may have a specific landmark (e.g., an off-center dot or line), such that coordinates of the pixel(s) covering the landmark in the first image may be assigned to the pixel(s) covering the same landmark in the other images. In other cases, the image itself can be considered as a feature for future alignment.

At 406, a second digital image is captured at time $t_x$. Time $t_x$ is a time after $t_0$ at which the bacteria in the imaged plate has had an opportunity to form visible colonies.

At 408, the second digital image is aligned with the first digital image based on the previously assigned coordinates. Aligning the images may further involve normalization and standardization of the images, for instance, using the methods and systems described in PCT Publication No. WO2015/114121.

At 410, contrast information of the second digital image is determined. The contrast information may be gathered on a pixel-by-pixel basis. For example, the pixels of the second digital image may be compared with the corresponding pixels (at the same coordinates) of the first digital image to determine the presence of temporal contrast. Additionally, adjacent pixels of the second digital image may be compared with one another, or with other pixels known to be background pixels, to determine the presence of spatial contrast. Changes in pixel color and/or brightness are indicative of contrast, and the magnitude of such changes from one image to the next or from one pixel (or region of pixels) to the next, may be measured, calculated, estimated, or otherwise determined. In cases where both temporal contrast and spatial contrast are determined for a given image, an overall contrast of a given pixel of the image may be determined based on a combination (e.g., average, weighted average) of the spatial and temporal contrasts of that given pixel.

At 412, objects in the second digital image are identified based on the contrast information computed at 410. Adjacent pixels of the second digital image having similar contrast information may be considered to belong to the same object. For instance, if the difference in brightness between the adjacent pixels and their background, or between the pixels and their brightness in the first digital image, is about the same (e.g., within a predetermined threshold amount), then the pixels may be considered to belong to the same object. As an example, the system could assign a "1" to any pixel having significant contrast (e.g., over the threshold amount), and then identify a group of adjacent pixels all assigned "1" as an object. The object may be given a specific label or mask, such that pixels with the same label share certain characteristics. The label can help to differentiate the object from other objects and/or background during later processes of the subroutine 400. Identifying objects in a digital image may involve segmenting or partitioning the digital image into multiple regions (e.g., foreground and background). The goal of segmentation is to change the image into a representation of multiple components so that it is easier to analyze the components. Image segmentation is used to locate objects of interest in images.

At 414, the features of a given object (identified at 412) may be characterized. Characterization of an object's features may involve deriving descriptive statistics of the object (e.g., area, reflectance, size, optical density, color, plate location, etc.). The descriptive statistics may ultimately quantitatively describe certain features of a collection of information gathered about the object (e.g., from a SHQI image, from a contrast image). Such information may be evaluated as a function of species, concentrations, mixtures, time and media. However, in at least some cases, characterizing an object may begin with a collection of qualitative information regarding the object's features, whereby the qualitative information is subsequently represented quantitatively. Table 1 below provides a list of example features that may be qualitatively evaluated and subsequently converted to a quantitative representation:

TABLE 1

Qualitative Attributes of Objects, and Criteria for Quantitatively Converting the Attributes

| Number | Feature | Score | Criteria |
|---|---|---|---|
| 1 | Growth | 0 | No growth |
| | | 1 | Growth |
| 2 | Expected Time to Visually Observe | n/a | Record time in hours |
| 3 | Size (diameter) | 1 | <1 mm |
| | | 2 | >1-4 mm |
| | | 3 | >4 mm |
| 4 | Growth Rate (Δ diameter/2 hrs) | 1 | <1 mm |
| | | 2 | >1-2 mm |
| | | 3 | >2 mm |
| 5 | Color | 1 | grey/white |
| | | 2 | rose-pink |
| | | 3 | colorless |
| | | 4 | red |
| | | 5 | blue |
| | | 6 | blue-green |

TABLE 1-continued

Qualitative Attributes of Objects, and Criteria for Quantitatively Converting the Attributes

| Number | Feature | Score | Criteria |
|---|---|---|---|
| | | 7 | brown |
| | | 8 | pale yellow to yellow |
| | | 9 | green |
| 6 | Hemolysis | 0 | none |
| | | 1 | small beta (<1 mm) |
| | | 2 | large beta (>1 mm) |
| | | 3 | alpha |
| 7 | Shape | 1 | convex |
| | | 2 | flat |
| | | 3 | spread |
| | | 4 | Concave |
| 8 | Surface/Edge | 1 | smooth |
| | | 2 | rough |
| | | 3 | mucoid |
| | | 4 | feet |

Some features of an object, such as shape or the time until it is observed visually, may be measured a single time for the object as a whole. Other features may be measured several times (e.g., for each pixel, for every row of pixels having a common y-coordinate, for every column of pixels having a common x-coordinate, for every ray of pixels having a common angular coordinate, for a circle of pixels having a common radial coordinate) and then combined, for instance using a histogram, into a single measurement. For example, color may be measured for each pixel, growth rate or size for every row, column, ray or circle of pixels, and so on.

At 416, it is determined whether the object is a colony candidate based on the characterized features. The colony candidate determination may involve inputting the quantitative features (e.g., the scores shown in Table 1, above), or a subset thereof, into a classifier. The classifier may include a confusion matrix for implementing a supervised machine learning algorithm, or a matching matrix for implementing an unsupervised machine learning algorithm, to evaluate the object. Supervised learning may be preferred in cases where an object is to be discriminated from a limited set (e.g., two or three) of possible organisms (in which case the algorithm could be trained on a relatively limited set of training data). By contrast, unsupervised learning may be preferred in cases where an object is to be discriminated from an entire database of possible organisms, in which case it would be difficult to provide comprehensive—or even sufficient—training data. In the case of either confusion or a matching matrix, differentiation could be measured numerically on a range. For instance, for a given pair of objects, a "0" could mean the two objects should be discriminated from each other, whereas a "1" could mean that the objects are difficult to differentiate one from the other.

Colony candidates may be stored in a memory of the automated system for further use (e.g., testing, the segmentation routine described below, etc.).

Use of Multiple Media

In the above examples, evaluation of a culture is described for a single media. However, the examples are similarly applicable to instances where a culture is evaluated in multiple media.

Since the characteristics of bacteria (e.g., color, growth rate, etc.) may vary depending on the type of culture media ("media") used, different confusion matrices may be applied for each medium during the classification (e.g., 416 of subroutine 400). Thus, it is fully within reason that the classifier for one media would output a "0" for two objects, whereas a classifier for a different media would output a "1" for the same two objects. The collective results of the classifiers could then be evaluated together (manually or based on further machine-driven relationships) to arrive at an overall or final differentiation or classification for the objects.

Evaluation of multiple media may be implemented using a single container. The single container may be configured to hold multiple media (e.g., bi-plate, tri-plate quadplate, etc.) such that the multiple media may be imaged together at the same time. Alternatively, multiple media may be evaluated by streaking a culture sample in several containers, each container holding one or more media. Each of the multiple containers may then be subjected to the imaging routines described above. The information derived from each of the media (e.g., characterized features) may then be collectively inputted into the classifier in order to make an even more informed identification of the growth spotted in the various media.

Contrast Information

Figure 5:
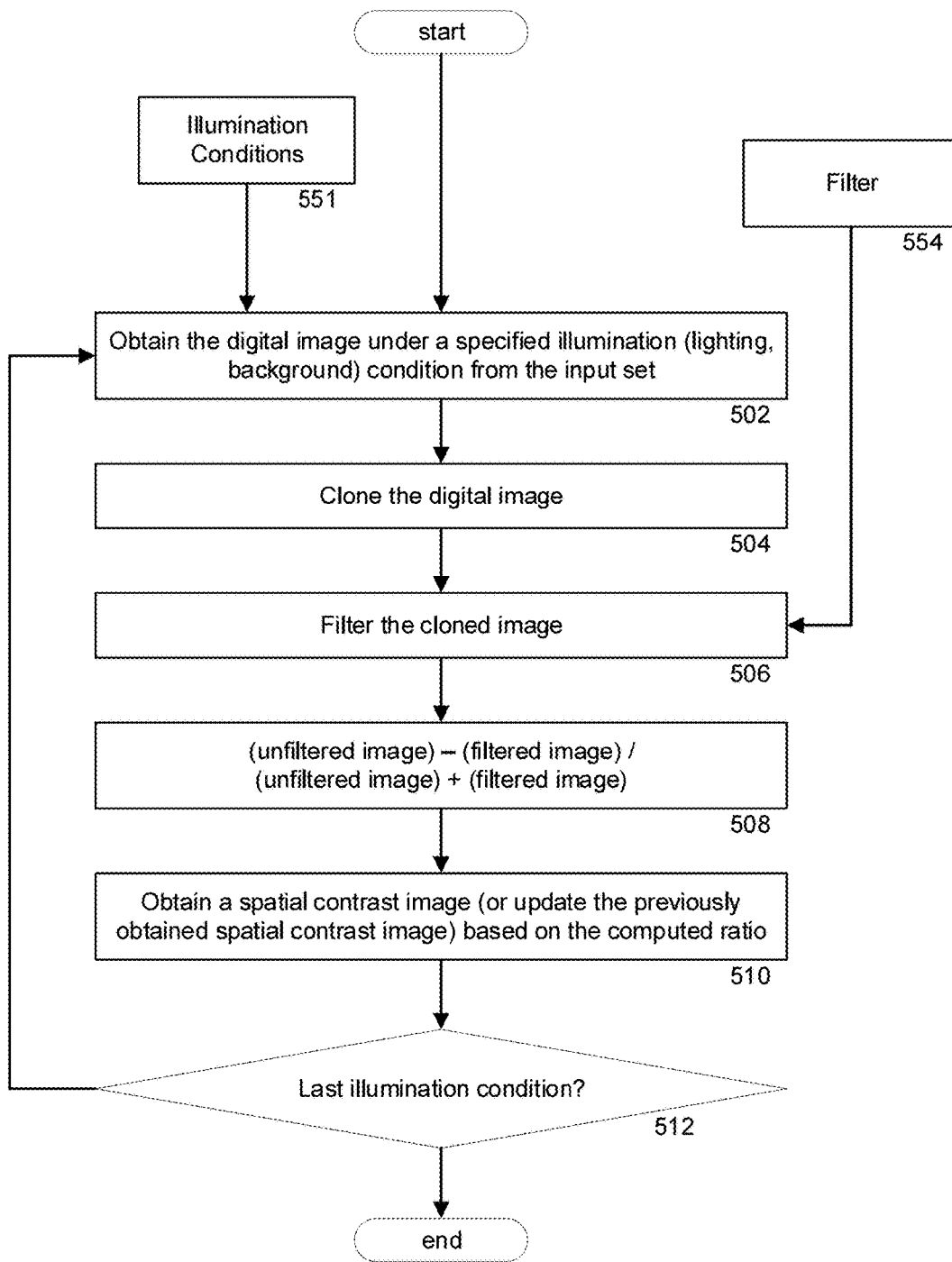
FIG. 5 is a flow chart of an example routine for obtaining spatial contrast according to an aspect of the disclosure.

FIG. 5 is a flow diagram showing an example subroutine 500 for obtaining spatial contrast as part of 410 of FIG. 4. The subroutine 500 receives as inputs: a set of one or more background and lighting conditions 551 and a filter 554. At 502, the digital image is obtained under a specified lighting and background condition from the input set 551. At 504, the image is then cloned. At 506, one of the cloned images is filtered using the filter 554. In the example of FIG. 5 a low pass kernel is used as the filter, but the skilled person is aware of other filters that might be used. At 508, a ratio of the filtered image subtracted from the unfiltered image, and the filtered image added to the unfiltered image, is computed. At 510, a spatial contrast image is obtained based on the computed ratio of 508. This routine 500 may be repeated for each of the background and lighting conditions 551. Each repetition of the routine 500 results in another spatial contrast image, which may be used to iteratively update the previously stored spatial contrast image at 510. Thus, a comprehensive contrast image (including contrast from each of the illumination conditions) may be iteratively built. In one embodiment, in each iteration, the cleared contrast image, in which the contrast settings are still set to zero (as compared to the iteratively built contrast image) may be provided as an input for each illumination setting. If it is determined at 512 that the last image has been processed, then routine 500 ends.

Figure 6:
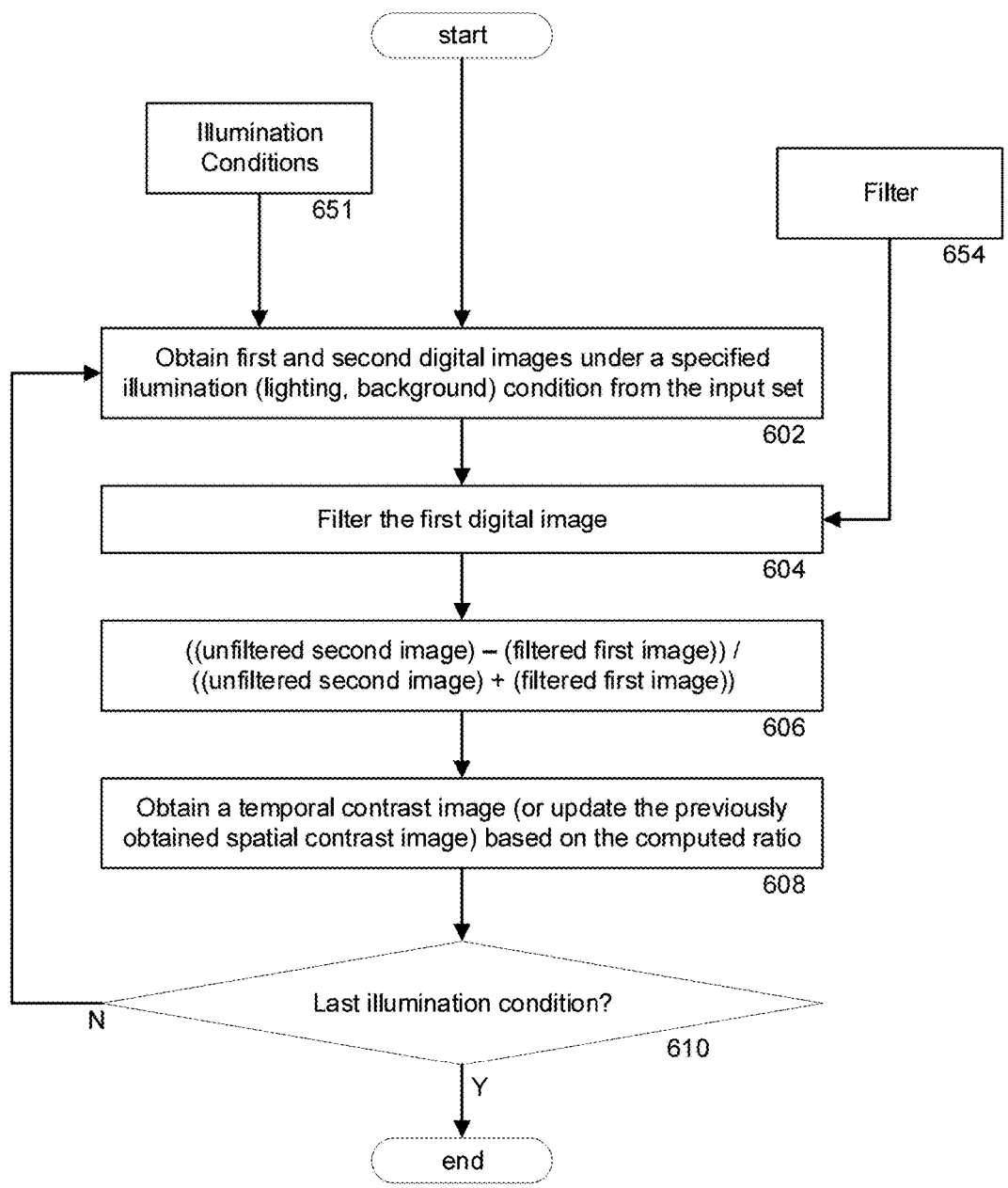
FIG. 6 is a flow chart of an example routine for obtaining temporal contrast according to an aspect of the disclosure.

FIG. 6 is a flow diagram showing an example subroutine 600 for obtaining temporal contrast also as part of 410 of FIG. 4. The subroutine 600 receives as inputs: a set of one or more background and lighting conditions 651; and a filter 655. At 602, each of the first and second digital images taken under specific lighting and background conditions is obtained. At 604, the to image is filtered. In the example of FIG. 6 a low pass kernel is used as the filter, but the skilled person is aware of other filters that might be used. At 606, a ratio of the filtered $t_0$ image subtracted from the unfiltered $t_x$ image, and the filtered $t_0$ image added to the unfiltered $t_x$ image, is computed. At 608, a temporal contrast image is obtained based on the computed ratio of 606. This routine 600 may be repeated under different illumination conditions and/or different background conditions. Each repetition of the routine 600 results in another temporal contrast image, which may be used to iteratively update the previously stored temporal contrast image at 608. As with the building of a spatial contrast image, a temporal contrast image may be built iteratively, with a cleared contrast image provided an input for each illumination condition. If it is determined at 610 that the last image has been processed, then routine 600 ends.

Spatial and temporal contrast results may further be combined in order to make a comprehensive or overall determination regarding contrast. The combination of spatial and temporal contrast is herein referred to as "mixed contrast" (MC). In one embodiment, mixed contrast may be derived from a spatial contrast (SC) image at time $t_0$, a spatial contrast image at time $t_x$, and a temporal contrast (TC) image derived from a comparison of $t_0$ and $t_x$ images, according to the following equation:

$$MC^{(t_0, t_x)} = \frac{TC^{(t_0, t_x)} + (SC^{t_x} - SC^{t_0})}{2} \quad (3)$$

Filtering

Additional processes may be included in the subroutine 400 of FIG. 4 in order to enhance the image analysis. For example, the first digital image may be analyzed for objects that appear in the image at time $t_0$. Since it is known that no bacteria have yet begun to significantly grow at $t_0$, it can be assumed that any objects spotted at time $t_0$ are merely dust, air bubbles, artifacts, condensation, etc. that would not constitute a colony candidate.

One filtering process could be used on a captured image to subtract dust and other artifacts that land on the imaged plate or lens. When considering transparent media (e.g., MacConkey's agar, CLED agar, CHROMagar, etc.), some level of dust is expected to be present on a captured image. The impact of the dust on a given image may be dictated at least in part based on the particular lighting and background conditions under which the image is taken. For example, when using white media, reflective artifacts and dust will be most observable when the media is illuminated from above with black background underneath. As another further example, when using colored or dark media, artifacts and dust will be most observable when the media is illuminated from above with a white background underneath. As a further example, in most any media, artifacts and dust that absorb light will be observable when the media is illuminated from underneath, regardless of background. In any case, management of dust and artifacts is a complex image processing challenge that can significantly impact detection of microbial growth.

Dust and artifacts can be broken down into two types: (A) those that are capable of changing position; and (B) those that are not capable of changing position. Dust and artifacts can accumulate over time, meaning the number of both types A and B may vary over time. Nonetheless, observations have shown that type A is more prone to change in quantity over time than is type B. Of course, type A is also more prone to change, such as due to the plate being moved into or out of the imaging chamber.

Generally, type B is caused by artifacts that are linked to the plate itself, such as ink dots (brand, lot number and information printed underneath the plate), imperfections linked to the plastic mold injection point, or a frosted region. Type B can also be caused by dust or air bubbles stuck on top of the media, trapped inside the media, or electrostatically stuck to the underside of the plate.

From an imaging point of view, even type A dust and artifacts are by themselves mostly unchanging in position. However, due to the plastic of the plate and the media acting as a filter and lens, the observed characteristics and position of the type A artifacts may change slightly depending upon the media color, the media level, and the plastic. Type B dust and artifacts are also unchanging in position. However, to the extent that type B dust and artifacts are connected to the media, and the media is subject to slighting movement and shifting over time (mostly due to slight desiccation over time in the incubator), the type B dust and artifacts can move with the media. Therefore, the position of type B dust and artifacts is also at least somewhat prone to subtle changes.

In terms of contrast, a speck of type A dust can be said to be present in the $t_0$ spatial contrast image at a position "$p_0$," and in the $t_x$ spatial contrast image at a position "$p_x$." Assuming $p_0$ and $p_x$ are different locations, then the dust or artifact will also be present in a temporal contrast image at both locations (e.g., showing positive contrast in the $p_x$ location, and negative contrast in the $p_0$ location). By comparison, a speck of type B dust will be present in a common location of both spatial contrast images at times $t_0$ and $t_x$, yet absent from the temporal contrast image.

As explained above, spatial and temporal contrast images can be combined in order to derive mixed contrast results. The impact of both types A and B dust and artifacts can further be eliminated from the mixed contrast results. In one embodiment, if an object (e.g., a CFU candidate) is identified in the mixed contrast result, it may be compared to the dust and artifacts detected with the neighborhood N(x,y) of the object in the spatial contrast result at time $t_0$. Then, if a similar object is found in the spatial contrast result at time $t_0$, the object identified in the mixed contrast result is flagged as an A type or B type false positive. Even if an object is not flagged as an A type or B type false positive at first, if over time the object is found to not significantly change size, it may still later be determined that the object is a B type false positive. The false positives may be stored, and later applied to subsequent images, such as through the filtering masks (e.g., binary mask) described further below.

Another filtering process could be used to subtract condensation formed on the plate (e.g., during transit from fridge to incubator at the beginning of an incubation session). In one example condensation filter, the plate is illuminated using bottom lighting, so that less light penetrates through locations of condensation than locations without condensation. The optical density of the image may then be evaluated, and areas of low optical density could be subtracted from the image.

Figure 7:
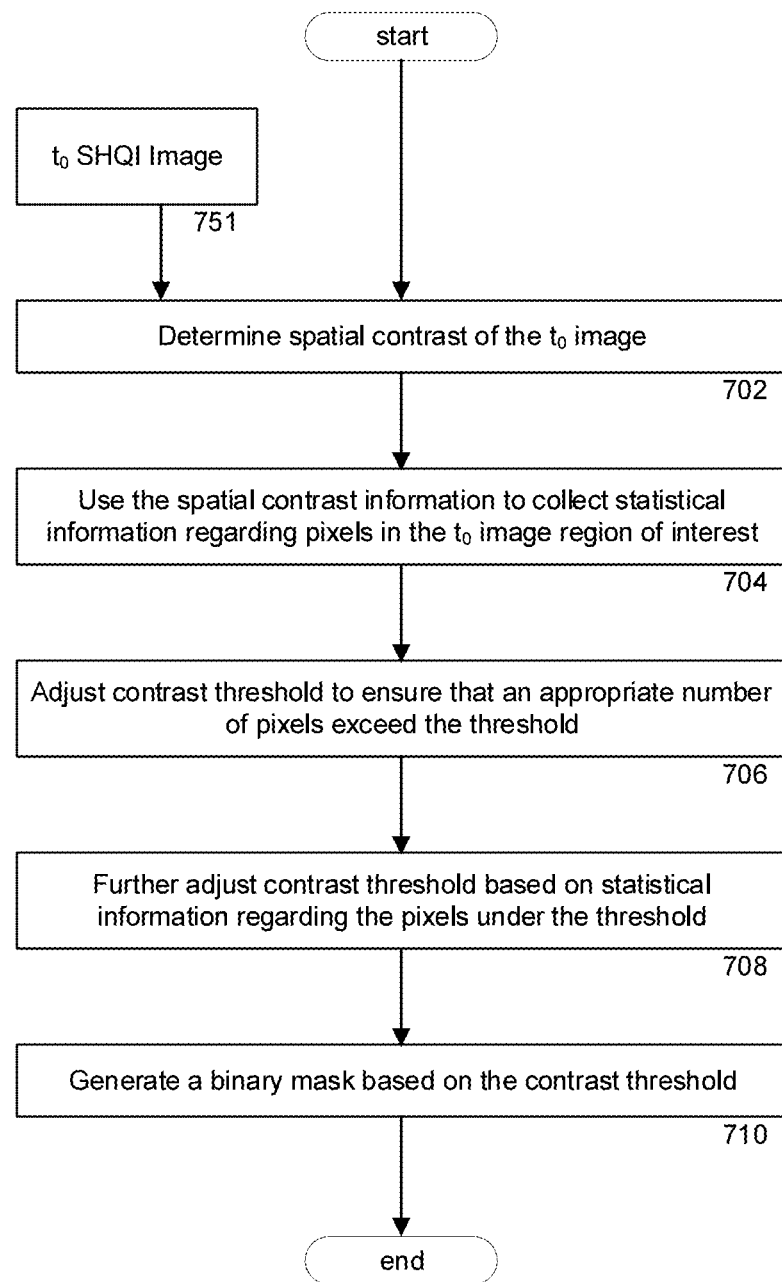
FIG. 7 is a flow chart of an example routine for filtering artifacts from an image according to an aspect of the disclosure.

Additionally or alternatively, an image mask could be constructed to discount objects from any analysis of the $t_0$ image and/or subsequent digital images. FIG. 7 is a flow diagram showing an example routine 700 for creating an image mask using spatial contrast of the $t_0$ image. In the example of routine 700, the only input provided is the SHQI image 751 taken at time $t_0$. At 702, spatial contrast of the $t_0$ image is determined. At 704, the spatial contrast information is used to collect statistical information regarding the pixels in the region of interest of the $t_0$ image, such as mean and standard deviation (e.g., of brightness). At 706, a contrast threshold is adjusted to ensure that an appropriate number of pixels exceed that threshold. For example, if more than a given percentage of pixels are not deemed background of the image, then the threshold may be increased. At 708, the threshold is further adjusted based on statistical information regarding those pixels under the threshold. Finally, at 710, a binary mask is generated. The binary mask differentiates between various artifacts that are not valid pixels, and other pixels which are considered valid. The binary mask could then be used at a subsequent time when there are potential colonies to detect, and to rule out objects occupying the not-valid pixels from being candidate colonies.

The above filtering processes could improve subroutine 400, by avoiding accidental inclusion of dust, condensation, or other artifacts as objects, and speeding up the property characterization at 414 since such characterization would only have to be performed for valid pixels.

Defining Objects and Labels

Figure 8:
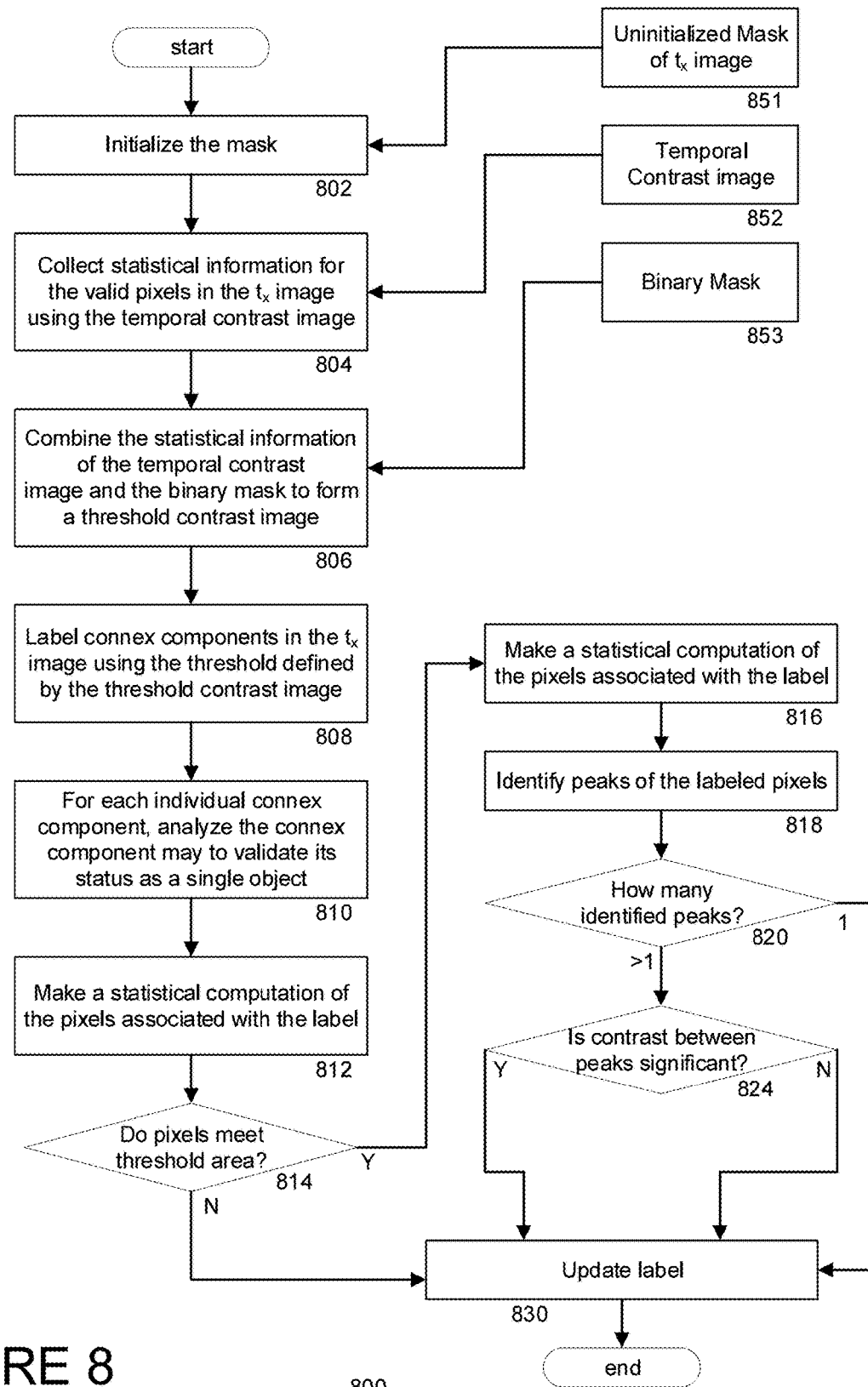
FIG. 8 is a flow chart of an example routine for labeling pixels of an image according to an aspect of the disclosure.

Another process that may be added to subroutine 400 of FIG. 4 is assigning labels to the objects identified at 412. The object may be given a specific label, such that pixels with the same label share certain characteristics. The label can help to differentiate the object from other objects and/or background during later processes of the subroutine 400. FIG. 8 is a flow diagram showing an example routine 800 for labeling the pixels of an image taken at time $t_x$ (or "$t_x$ image"). In the example of FIG. 8, a binary mask 851 (e.g., the output of routine 700), an uninitialized candidate mask 852 for the $t_x$ image, and a temporal contrast image 853 (e.g., the output of subroutine 600) are received as inputs. At 802, the candidate mask 852 is initialized. Initialization may involve identifying a region of interest on the imaged plate, as well as using the binary mask 851 to identify "valid pixels" in the image taken at time $t_x$. Valid pixels are pixels of the imaged that have not been discounted as candidate colonies, and will be considered for labeling. At 804, the temporal contrast image 853 is used to collect statistical information regarding the valid pixels in the region of interest of the $t_x$ image, such as mean and standard deviation (e.g., of brightness). Then, at 806, the statistical information of each of the temporal contrast image 853 and the binary mask 851 (which are preferably generated under similar lighting and background conditions) are combined to form a threshold contrast image. Using the threshold defined by the threshold contrast image, "connex components" of the $t_x$ image are labeled at 808. A connex component is effectively a label indicating a connection between (or grouping among) adjacent pixels, which in turn indicates that the pixels are part of the same object.

Once the connex components have been defined for the tx image, each connex component may be individually analyzed (at 810) to validate its status as a single object. In the example of FIG. 8, a statistical computation of the pixels associated with the label is made at 812. The computation may utilize a histogram to determine mean and/or standard deviation of brightness or color of the pixels. At 814, it is determined whether the pixels meet a threshold area. If the threshold area is not met, then operations proceed to 830, in which the label is updated. Updating a label may involve either keeping the analyzed component as one label, or dividing the component up into two labels. In the case of the threshold area not being met, the component is kept as a single label. If the threshold area is met, then at 816, the histogram is smoothed, and at 818, peaks of the distributed labeled pixels are identified. Peaks may be further defined by having a minimum area, since that peaks smaller than the minimum area may be disregarded. At 820, the number of identified peaks is counted. If there is only one peak, then operations proceed to 830, and the label is updated, whereby the component is kept as one object. If there is more than one peak, then at 824, the threshold contrast image is used to further assess whether the contrast between the peaks is significant. Operations then proceed to 830, and the label is updated based on the multiple identified peaks, whereby significant contrast results in the component being divided into two, and otherwise being kept as one.

Segmentation

Another process that may be included as part of subroutine 400 is a segmentation process for separating confluent colonies at time $t_x$ into separate objects. If at time $t_x$ the colonies have grown to the point where they overlap or touch one another, it may be required to draw a boundary through the confluent region in order to evaluate separate colonies in the region.

Figure 9:
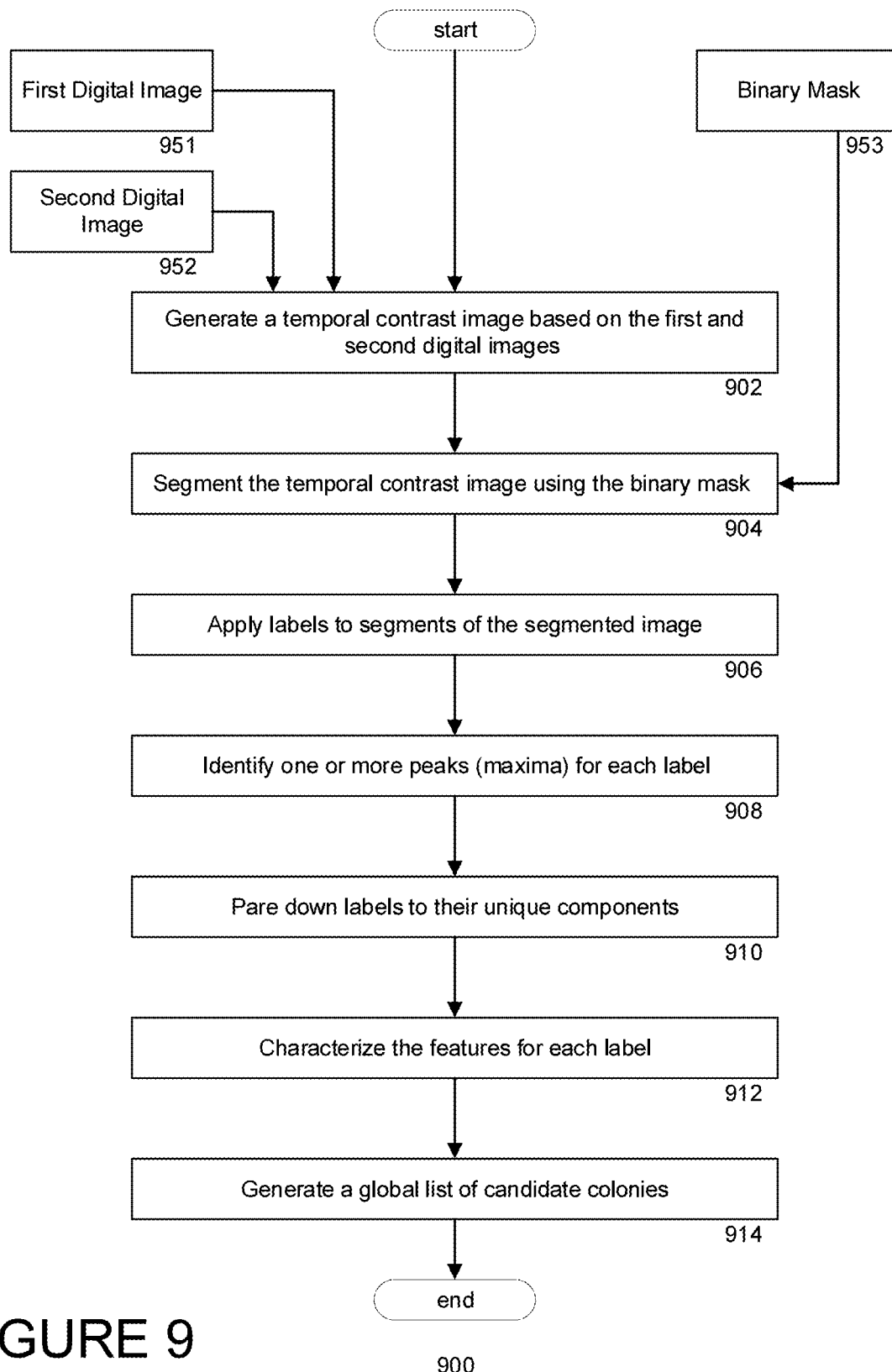
FIG. 9 is a flow chart of an example routine for separating colonies into separate objects according to an aspect of the disclosure.

In some instances, where two bordering colonies have different features (e.g., different color, different texture), segmentation may simply involve feature analysis of the confluent region. However, spatial and temporal contrast alone are not always enough to identify a boundary between the colonies. FIG. 9 is a flow diagram showing an example routine 900 for separating such colonies into separate objects (e.g., with separate labels), or in other terms, segmenting the colonies. The example routine 900 of FIG. 9 uses a first digital image 951 taken at time $t_0$, a second digital image taken at time $t_x$ and a $t_0$ image binary mask 953 (e.g., the mask generated by routine 700) as inputs. At 902, a temporal contrast image is generated based on the $t_0$ and $t_x$ images 951 and 952. At 904, the temporal contrast image is segmented using the binary mask 953. At 906, labels are applied to the segments of the image. At 908, peaks or maxima of each label are identified. The maximum of a given segment is generally the centerpoint or center of mass of the segment. At 910, for each label, the maxima (e.g., of the label under analysis, of neighboring labels) are used make further determinations as to whether a given label is unique to its neighbors, or should be combined with one or more neighboring labels. Once the labels have been pared down to their unique components, characterization of the features for each label (e.g., steps 414 and 416 of routine 400) may be performed at 912, and a global list of candidate colonies may be generated at 914.

Various factors, such as inclusion factors, may be applied to determine if local maxima of a given label belong to one colony or to different colonies. Inclusion factors are factors that indicate whether or not neighboring pixels are associated with an adjacent object. Such factors may be used in a segmentation strategy to determine whether to split two local maxima in a given label into two separate objects, or merge them into a single object.

Figure 10:
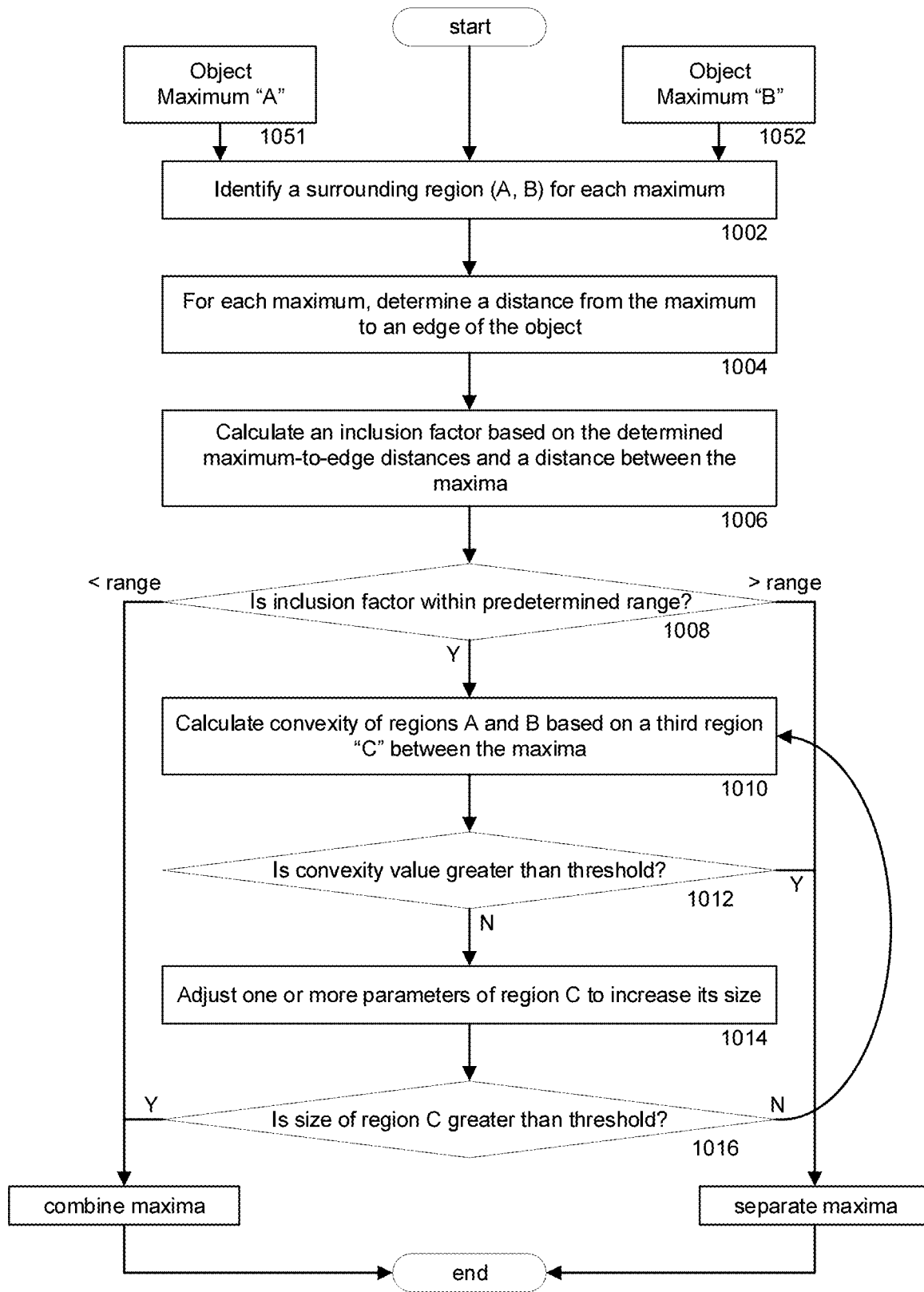
FIG. 10 is a flow chart of an example object segmentation routine according to an aspect of the disclosure.
Figure 11:
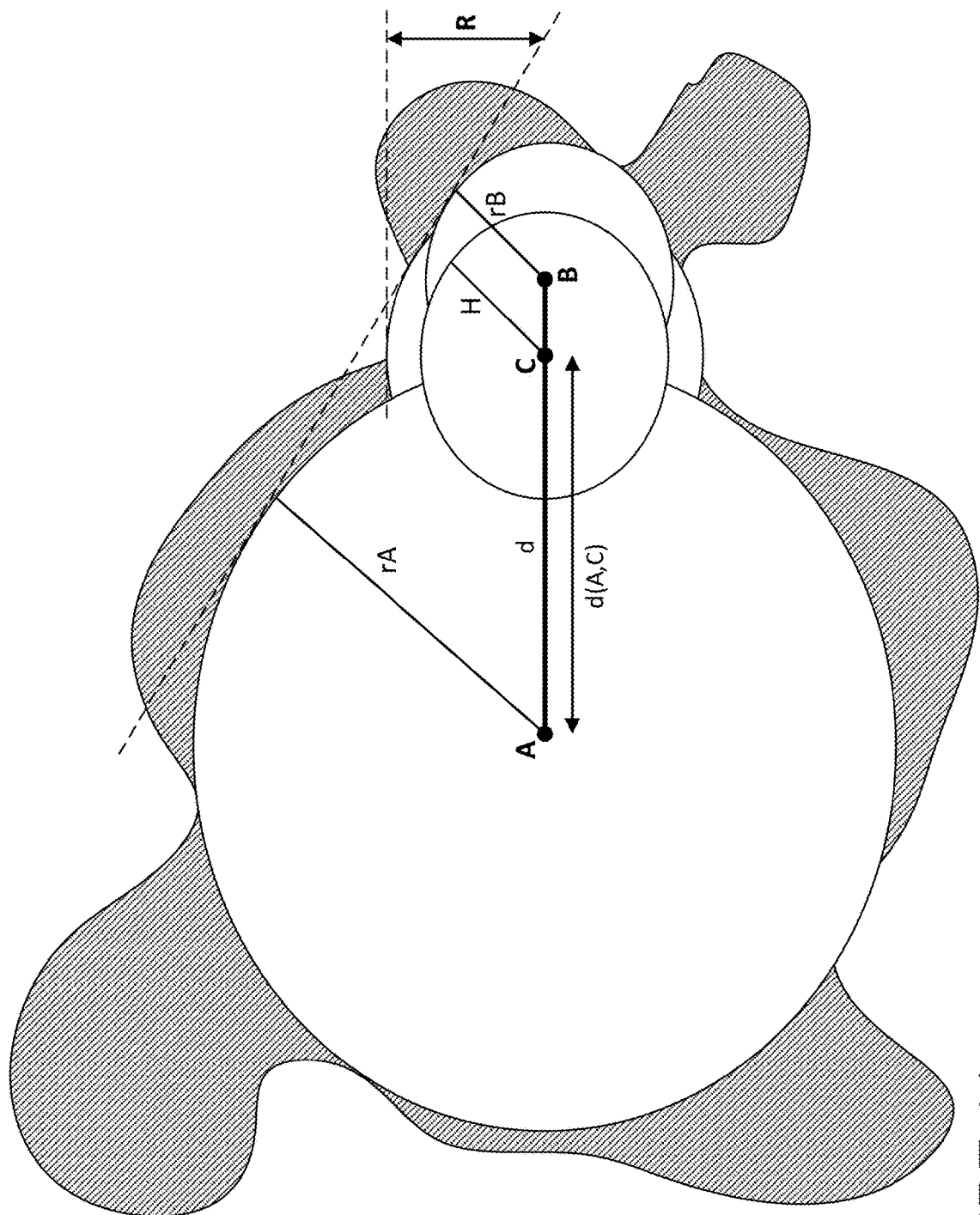
FIG. 11 is an illustration showing measurements of confluent colonies as part of the segmentation routine of FIG. 10.

FIG. 10 is a flow diagram showing such an example segmentation strategy. The routine 1000 may be used as a subroutine of step 910 in FIG. 9. As shown in FIG. 10, two local maxima 1051 and 1052 are identified. At 1002, a surrounding region is identified for each maximum. In the example of FIG. 10, region "A" surrounds maximum 1051, and region "B" surrounds maximum 1052. For purposes of the example equations below, it is assumed that region A is larger or equal in size to region B. In some instances, each region may be given an oval shape having a horizontal distance (xA, xB) along a horizontal axis of the region and a vertical distance (yA, yB) along a vertical axis of the region. FIG. 11 provides an example illustration of regions A and B and their respective maxima in order to clarify the routine of FIG. 10.

At 1004, a distance from the maximum to an edge of the object is determined for each local maximum 1051 and 1052. In some instances, the determined distance is an either an average or median distance of the region assigned at 1002, hereinafter referred to as a distance map. The distance map of region A is hereinafter referred to as rA, and that of region B as rB.

At 1006, an inclusion factor is calculated based on a distance "d" between the two local maxima and the distances determined at 1004. In one embodiment, the inclusion factor is calculated using the following equation:

$$\text{Inclusion Factor} = \frac{d - rA + rB}{2rB} \qquad (4)$$

At 1008, it is determined whether the inclusion factor is less than, greater than, or within a predetermined range (e.g., between 0.5 and 1). If the inclusion factor is less than the predetermined range, the maxima are determined to be associated with the same object. If it is greater than the predetermined range, the maxima are determined to be associated with separate objects.

For inclusion factors falling within the range, it is not immediately clear whether the maxima belong to the same or different objects, and more processing is needed. The routine 1000 then continues at 1010, in which the convexity of the respective surrounding regions of the two maxima is calculated using the coordinates of a third region "C" at a position between the two maxima. In some instances, the region may be a weighted center of the two regions, such that the center point of region C is closer to the smaller region B than to the larger region A. Horizontal and vertical distances xC and yC, and a distance map H, may also be calculated for region C. For example, the convexity may be calculated using the above values and d(A,C), which is the distance between the center points of region C and maximum A, according to the following equations:

$$xC = \frac{xA + (xB - xA) * distOffset}{d} \qquad (5)$$

$$yC = \frac{yA + (yB - yA) * distOffset}{d} \qquad (6)$$

$$R = rA + (rB - rA) * \frac{d(A, C)}{d} \qquad (7)$$

$$\Delta H = H - (0.9R) \qquad (8)$$

At 1012, it is determined whether the convexity value is greater (more convex) than a given threshold. For example, ΔH may be compared to a threshold value of 0. If convexity value is greater than the threshold value, the maxima are determined to be associated with separate objects. Otherwise, at 1014, one or more parameters of region C are updated such that the size of region C is increased. For example, distOffset may be updated based on ΔH, e.g., ΔH is capped at a value between 0 and 1 (if ΔH is greater than 1, it is rounded to 1) and is then added to distOffset.

At 1016, it is determined whether the size of region C meets or exceeds a threshold value. If this threshold value is met or exceeded, then the maxima are determined to be associated with the same object. In other words, if the difference between regions A and B is so indetermination that region C is increased until it begins to overshadow regions A and B, this is a good indication that maxima 1051 and 1052 should belong to the same object. In the above example, this may be indicated by distOffset meeting or exceeding the distance d between the maxima. Otherwise, operations return to 1010, and convexity of regions A and B are re-calculated based on the updated parameter(s) of region C.

Once the associations for every maximum are determined, the determined associations may be stored, for example in a matrix (also referred to as an association matrix). The stored information may be used to reduce the full list of maxima to a final list of candidate objects. For instance, in the case of an association matrix, a master list may be created from the full list of maxima, and then each maximum may be iteratively reviewed and removed from the master list if an associated maximum still remains on the list.

In the example of FIGS. 9 and 10, the time $t_x$ at which the second image is taken (and, thus, the earliest time that the routine 900 may be executed) may be only a few hours into the incubation process. Such a time is generally considered too early to identify fully formed colonies, but may be sufficient for creating a segmentation image. The segmentation image may optionally be applied to future images which are taken at a subsequent time. For example, boundaries between colonies may be drawn to predict an expected growth of the colonies. Then, in a case of confluence among the colonies, the boundaries may be utilized to separate confluent colonies.

Analysis with Two or More Images after Time $T_0$

While the above described processes and routines require only one image taken after time $t_0$ (e.g., a first digital image at time $t_0$ and a second digital image at time $t_x$), other processes require at least a second image taken after time $t_0$. For example, if it is discovered that the image at time $t_x$ includes confluent colonies, another image taken at time $t_n$ (in which 0<n<x) may be used to identify and split up the individual colonies.

For instance, if $t_0$=0 hours into incubation (at which time no growth has occurred) and $t_x$=24 hours into incubation (at which time so much growth has occurred that colonies are now confluent), an image at time $t_n$=12 hours (at which time the colonies would have begun to grow but not yet be confluent) would reveal the presence of individual colonies. Colony growth could then be projected based on the image at time $t_n$ to estimate boundaries between the confluent colonies at time $t_x$. In this regard, the image at time $t_n$ could help to differentiate a fast growing colony from a slow growing colony. Those skilled in the art should recognize that as the number of images taken between time $t_0$ and time $t_x$ increases, the more accurately the growth rate of the colonies may be projected.

In one application of the foregoing concept, the image taken at time $t_n$ (or more generally, images taken between times $t_0$ and $t_x$) could be used to identify colony seeds, which are objects suspected of being colonies that will grow over time, and associate the seeds with corresponding masks and labels. Each seed would receive a unique label and the label would be stored along with different features (e.g., position, morphological, and histogram based on images generated from SHQI images: red channel, green channel, blue channel, luminance, chrominance, hue or composite image) and properties (e.g., isolated/non-isolated status, other information for projecting chronological propagation). Some stored features (e.g., histogram) may also be computed at the plate level, instead of being attributed to a specific seeds, in order to extract plate global indicators. The seeds stored features could then be used to perform colony extraction at time $t_x$, as well as being provided as input to the classifiers for training and/or testing.

Growth rate tracking using multiple images taken after to could also be used to detect dust, artifacts, or other foreign objects which appear on the plate or in the imaging lens in the middle of the workflow routine. For instance, if a speck of dust were to land on the imaging lens after to but before $t_n$, the spot created by the speck could initially be interpreted as a growing colony since it was not visible at time $t_0$. However, with subsequent imaging revealing no change in size to the spot, it may be determined that the spot is not growing, and therefore not a colony.

Aside from tracking growth rate and segmentation, other aspects of the colonies may be tracked with the help of additional images between $t_0$ and $t_x$. In the case of subtle morphological changes that develop in a colony slowly over time, those subtle changes could be identified quicker by capturing more images. In some cases, growth could be measured along a z-axis, in addition to or instead of along the usual x- and y-axes. For instance, *Streptococcus pneumonia* is known to slowly form a sunken center when grown in blood agar, but the sunken center is generally not visible until the second day of analysis. By looking at a time progression of the bacteria growth, an incipient sinking center may be detected and the bacteria identified much earlier than if one must wait for the center to completely sink.

In other cases, a colony could be known to change color over time. Therefore, imaging of a colony having a first color (e.g., red) at a time after $t_0$, and then having a second color (e.g., green) at a subsequent time, could be used to determine the identity of the bacteria growing in the colony. Color change could be measured as a vector or path through color space (e.g., RGB, CMYK, etc.) Changes to other chromatic features of the colony could be similarly measured.

Object Features

As discussed above in connection with FIG. 4, features of an object on an imaged plate may be characterized as part of the image analysis performed on the imaged plate. The characterized features may include both static features (pertaining to a single image) and dynamic image (pertaining to a plurality of images).

Static features aim at reflecting object attributes and/or surrounding background at a given time. Static features include the following:

Center of gravity: this is a static feature that provides a center of gravity of an imaged object in a coordinate space (e.g., x-y, polar). The center of gravity of an object, like the polar coordinates of the object, provides invariance in the feature set under given lighting and background conditions. The center of gravity may be obtained by first determining a weighted center of mass for all colonies in the image (M being the binary mask of all detected colonies). The weighted center of mass may be determined based on an assumption that each pixel of the image is of equal value. The center of gravity for a given colony may then be described in x-y coordinates by the following equation (in which E={p|p∈M} (E is the current colony's binary mask), the range for the x-coordinate is [0, image width], the range for the y-coordinate is [0, image height], and each pixel is one unit):

$$igv_{(x,y)}\left(x = \frac{1}{\sum_{p \in E} 1} \times \sum_{p \in E} p_x, y = \frac{1}{\sum_{p \in E} 1} \times \sum_{p \in E} p_y\right) \quad (9)$$

(ii) Polar coordinates: this is also a static feature, and can be used to further characterize locations on the imaged plate, such as a center of gravity. Generally, polar coordinates are measured along a radial axis (d) and an angular axis (θ), with the coordinates of the plate center being [0,0]. Coordinates d and θ of $igv_{(x,y)}$ are given (in millimeters for d, and in degrees for θ) by for following equations (Where k is a pixel density corresponding pixels to millimeters, and "barcode" is a landmark feature of the imaged plate to ensure alignment of the plate with previous and/or future images):

$$d = k \times \text{dist}(igv_{(x,y)}, 0_{(x,y)}) \quad (10)$$

$$\theta = \text{Angle}(\text{barcode}, 0_{(x,y)}, igv_{(x,y)}) \quad (11)$$

(iii) Image vector: The two-dimensional polar coordinates may in turn be transformed into a one-dimensional image vector. The image vector may characterize intensity of the pixels of an image as a function of the radial axis (generally, with the center of the colony having the highest intensity) and/or a function of the angular axis. In many cases, the image vector may be more accurate at classifying similarities/distinctions among imaged objects.

(iv) Morphometric features, which describe the shape and size of a given object.

(a) Area: This is a morphometric feature, and can be determined based on the number of pixels in the imaged object (also referred to as a "blob"), not counting holes in the object. When pixel density is available, area may be measured in physical size (e.g., mm²). Otherwise, when pixel density is not available, the total number of pixels may indicate size, and pixel density (k) is set to equal one. In one embodiment, area is calculated using the following equation:

$$A = k^2 \times \Sigma_{p \in E} 1 \quad (12)$$

(b) Perimeter: The perimeter of the object is also a morphometric feature, and can be determined by measuring the edges of the objecting and adding together the total length of the edges (e.g., a single pixel having an area of 1 square unit has a perimeter of 4 units). As with area, length may be measured in terms of pixel units (e.g., when k is not available) or physical lengths (e.g., when k is available). In some circumstances, the perimeter may also include the perimeter of any holes in the object. Additionally, the ladder effect (which results when diagonal edges are digitized into ladder-like boxes) may be compensated by counting inside corners as $\sqrt{2}$, rather than 2. In one embodiment, perimeter may be determined using the following equations:

$$P = k \times \sum_{p \in E} q(n_p) \quad (13)$$

$$n_p = \begin{Bmatrix} t \\ l & p & r \\ & b & \end{Bmatrix} \quad (14)$$

if: $\left\{\sum (t \in M, l \in M, r \in M, b \in M) = 2, \right.$ (15)
$(l \in M \neq r \in M), (t \in M \neq b \in M)\}$
(p is interior and p is a corner)
then: $q(n_p) = \sqrt{2}$
else: $q(n_p) = 4 - \sum(t \in M, l \in M, r \in M, b \in M)$ (c) Circularity: The circularity of the object is also a morphometric feature, and can be determined based on a combination of the area and perimeter. In one embodiment, circularity is calculated using the following equation:

$$C = \frac{4\pi A}{p^2} \quad (16)$$

(d) Radius Coefficient of Variation (RCV): This is also a morphometric feature, and is used to indicate variance in radius of the object by taking a ratio between the mean radius $\overline{R}$ of the object in all N directions or angles θ extending from the center of gravity and standard deviation of the radii $\sigma_R$. In one embodiment, this value can be calculated using the following equations:

$$\overline{R} = \frac{\sum_{\theta=0}^{2\pi} R_\theta}{N_\theta} \quad (17)$$

$$\sigma_R = \sqrt{\frac{\sum_{\theta=0}^{2\pi}(R_\theta - \overline{R})^2}{N_\theta - 1}} \quad (18)$$

$$RCV = \frac{\sigma_R}{\overline{R}} \quad (19)$$

(v) Contextual features, which describe the neighborhood topographical relationships of the object under scrutiny to the other detected objects and plate walls edges. For example, in the case of an imaged colony, one contextual feature of the colony may be whether the colony is free, has limited free space, or is competing for access to resources with other surrounding colonies. Such features tend to help classify colonies growing in the same perceived environment, and/or discriminating colonies growing in different environments.

Figure 12:
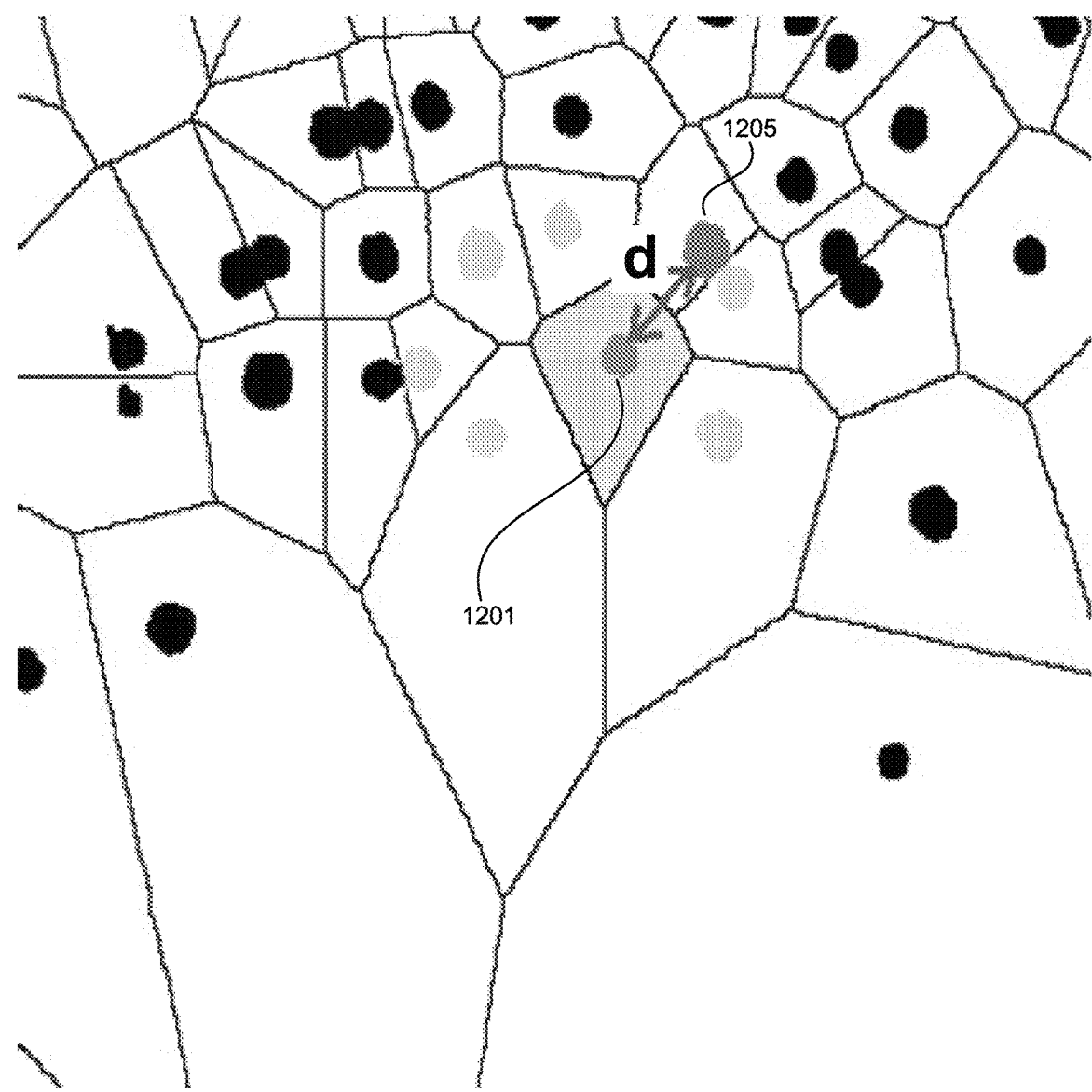
FIG. 12 is a Voronoï diagram according to an aspect of the disclosure.

(a) Region of Influence: this is a contextual feature that considers the space between an object and its neighboring objects and predicts a region that the object under analysis may expend to occupy (without other, different objects expending to occupy that same region first). The region of influence can be expressed in the form of a Voronoï diagram, such as the diagram shown in FIG. 12, which shows a region of influence (shaded) based on the distance d between a colony 1201 and its neighboring colonies, e.g., 1205. In one embodiment, the distance from the edge of the object to the edge of the region of influence ($D_{NC}$) may be characterized using the following equation:

$$D_{NC} = k \times \text{Min}[\text{dist}(p \in E, \acute{p} \in M \in E)] \quad (20)$$

(b) Distance to Plate Wall: this is a contextual feature that calculates the distance of the edge of the object from the nearest plate wall ($D_{PW}$). In one embodiment, this distance may be characterized using the following equation:

$$D_{PW} = k \times \text{Min}[\text{dist}(p \in E, \dot{p} \in \text{Plate})] \quad (21)$$

(c) Isolation Factor: this is a contextual feature characterizing the relative isolation of a given object based on the object's size and distance to the nearest edge (e.g., of another object, a plate wall). FIGS. 13A-C illustrate aspects of isolation factor. FIG. 13A illustrates an instance in which the nearest edge is distance d from the colony to a plate wall. FIGS. 13B and 13C illustrate an instance in which the nearest edge belongs to another colony. In such a case, a circle is drawn centered around the colony under analysis and then expanded (first small, as in FIG. 13B, then larger as in FIG. 13C) until the circle touches a neighboring colony. In the embodiments of FIGS. 13A-C, the isolation factor (IF) may be characterized using the following equation:

$$IF = \frac{\text{Min}(D_{NC}, D_{PW})}{R} \quad (22)$$

(d) Neighboring Occupancy Ratio: this is a contextual feature characterizing the area fraction of a plate's bounded Voronoï region of influence (V) within a given distance d for a given object. In one embodiment, the neighboring occupancy ratio (OR) may be characterized using the following equation (in which for this equation, $$E = \{p \mid p \in V, \text{dist}(p, igv_{(x,y)}) < d\}): \quad (23)$$

$$OR(d) = \frac{k^2 \times \sum_{p \in E} 1}{\pi(d/2)^2}$$

(e) Relative Neighboring Occupancy Ratio: in some instances, the given distance d may be derived using the mean radius of the object multiplied by a predetermined factor ($d = x \times \overline{R}$). The result is a relative neighboring occupancy ratio (RNOR), and may be derived for a given factor x using the following equations:

$$RNOR(x) = NOR(d) \quad (24)$$

(vi) Spectral features, which describe the light properties of a given object. Color (red, green, and blue light channels; hue, luminance and chrominance, or any other color space transformation), texture and contrast (over time and/or across space) are examples of such features. Spectral features can be derived from images captured at various time points and/or under various illumination conditions during incubation using colony masks, and can further be associated with a Voronoï region of influence for a given colony.

(a) Channel Image: this is a spectral feature in which a specific color channel (e.g., red (R), green (G), blue (B)) is used to spectrally resolve the image.

(b) Luma: this is also a spectral feature used to characterize brightness of an image using RGB channels as an input.

(c) Hue: this is a spectral feature in which an area of the image is characterized as appearing to be similar to a perceived color (e.g., red, yellow, green, blue) or a combination thereof. Hue ($H_2$) is generally characterized using the following equations:

$$H_2 = \text{atan2}(\beta, \alpha) \quad (25)$$

$$\alpha = R - \frac{1}{2}(G + B) \quad (26)$$

$$\beta = \frac{\sqrt{3}}{2}(G - B) \quad (27)$$

(d) Chroma: this is a spectral feature for characterizing the colorfulness of an area of an image relative to its brightness if that area were similarly illuminated white. Chroma ($C_2$) is generally characterized using the following equation:

$$C_2 \sqrt{\alpha^2 + \beta^2} \quad (28)$$

(e) Radial Dispersion: analyzing radial dispersion of the hue and chroma contrast enables the discrimination of alpha, beta and gamma hemolysis.

(f) Maximum Contrast: this feature characterizes resolution of the image by computing the maximum of a measured average contrast for pixels at a given radius r from a central point of the image (e.g., the center of an imaged colony). This feature may be used to describe the perceptual differences between an image taken at times $t_0$ and $t_x$ based on the growth induced by the analyzed object. Maximum contrast may be characterized as follows:

$$\text{MaxContrast}_r = \text{MAX}(\text{AverageContrast}_r)_{object} \quad (29)$$

(vii) Background features, which describe alterations in the media in the neighborhood of the analyzed object. For instance, in the case of an imaged colony, the changes could be caused by microbial growth around the colony (e.g., signs of hemolysis, changes in PH, or specific enzymatic reactions).

Dynamic features aim at reflecting a change of object attributes and/or surrounding background over time. Time series processing allows static features to be related over time. Discrete first and second derivatives of these features provide instantaneous "speed" and "acceleration" (or plateauing or deceleration) of the change in such features to be characterized over time. Examples of dynamic features include the following:

(i) Time series processing for tracking the above static features over time. Each feature measured at a given incubation time may be referenced according to its relative incubation time $t_0$ allows for the features to be related ones measured at later incubation times. A time series of images can be used to detect objects such as CFUs appearing and growing over time, as described above. Time points for imaging may be preset or defined by an automated process based upon ongoing analysis of previously captured images of the objects. At each time point the image can be a given acquisition configuration, either for the entire series of a single acquisition configuration, or as a whole series of images captured from multiple acquisition configurations.

(ii) Discrete first and second derivatives of the above features for providing instant speed and acceleration (or plateauing or deceleration) of the changes to such features over time (e.g., tracking growth rate, as discussed above):

(a) Velocity: a first derivative of a feature over time. Velocity (V) of a feature x may be characterized in terms of (x units)/hour, with Δt being a span of time expressed in hours, based on the following equations:

$$V = \lim_{\Delta t \to 0} \left(\frac{dx}{dt}\right)^n \quad (30)$$

$$V_{1,0} = \frac{x_1 - x_0}{t_1 - t_0} \quad (31)$$

$$V_{2,1} = \frac{x_2 - x_1}{t_2 - t_1} \quad (32)$$

(b) Acceleration: a second derivative of the feature over time, also the first derivative of Velocity. Acceleration (A) may be characterized based on the following equation:

$$A = \lim_{\Delta t \to 0} \frac{dV}{dt} \quad (33)$$

The above image features are measured from the objects or the objects' context and aim at capturing specificities of organisms growing on various media and incubation conditions. The listed features are not meant to be exhaustive and any knowledgeable person in the field could modify, enlarge or restrict this feature set according to the variety of known image processing based features known in the field.

Image features may be collected for each pixel, group of pixels, object, or group of objects, in the image. A distribution of the collected features can be constructed in a histogram in order to more generally characterize regions of the image, or even the entire image. The histogram can itself rely on several statistical features in order to analyze or otherwise process the incoming image feature data.

Statistical histogram features can include the following:

(i) Minimum: the smallest value of the distribution captured within the histogram. This may be characterized by the following relationship:

$$\text{Min} = i \,|\, \{h(i) > 0, \Sigma_{j=0}^{j<i} h(i) = 0\} \quad (34)$$

(ii) Maximum: the largest value of the distribution captured within the histogram. This may be characterized according to the following relationship:

$$\text{Max} = i \,|\, \{h(i) > 0, \Sigma_{j=i+1}^{\infty *} h(i) = 0\} \quad (35)$$

(iii) Sum: the sum of all the individual values captured within the histogram. Sum may be defined by the following relationship:

$$\text{Sum} = \Sigma_{i=min}^{max} i \times h(i) \quad (36)$$

(iv) Mean: the arithmetic mean, or average. This is the sum of all the scores divided by the number of scores (N) according to the following relationship:

$$\text{Mean} = \frac{\sum_{i=min}^{max} i \times h(i)}{N} \quad (37)$$

(v) Quartile 1 (Q1): The score at the 25$^{th}$ percentile of the distribution. 25% of the scores are below Q1 and 75% are above Q1. This is described by the following relationship:

$$Q_1 = i \,\Big|\, \left\{\sum_{j=min}^{j<1} h(i) < \frac{N}{4}, \sum_{j=min}^{j \le i} h(i) \ge \frac{N}{4}\right\} \quad (38)$$

(vi) Median (Q2): The score at the 50$^{th}$ percentile of the distribution. 50% of the scores are below the median and 50% are above the median. The median is less sensitive to extreme scores than the mean and this generally makes it a better measure than the mean for highly skewed distributions. This is described by the following relationship:

$$\text{Median} = Q_2 = i \,\Big|\, \left\{\sum_{j=min}^{j<1} h(i) < \frac{N}{2}, \sum_{j=min}^{j \le i} h(i) \ge \frac{N}{2}\right\} \quad (39)$$

(vii) Quartile 3 (Q3): The score at the 75th percentile of the distribution. 75% percent of the scores are below Q3 and 25% are above Q3. This is described by the following relationship:

$$Q_3 = i \,|\, \{\Sigma_{j=min}^{j<i} h(i) < \tfrac{3}{4}N, \Sigma_{j=min}^{j \le i} h(i) \ge \tfrac{3}{4}N\} \quad (40)$$

(viii) Mode: The most frequently occurring score in a distribution. This is used as a measure of central tendency. The advantage of the mode as a measure of central tendency is that its meaning is obvious. Further, it is the only measure of central tendency that can be used with nominal data. The mode is highly subject to sample fluctuations and is therefore generally not used as the only measure of central tendency. Also, many distributions have more than one mode. These distributions are called "multimodal." Mode is described by the following relationship:

$$\text{Mode} = i \,|\, \{h(i) \ge h(i)_{i=min}^{max}\} \quad (41)$$

(ix) Trimean: A score computed by adding the 25th percentile plus twice the 50th percentile (median) plus the 75th percentile and dividing by four. The trimean is almost as resistant to extreme scores as the median and is less subject to sampling fluctuations than the arithmetic mean in skewed distributions. However, it is generally less efficient than the mean for normal distributions. Trimean is described according to the following relationship:

$$\text{TriMean} = \frac{Q_1 + 2Q_2 + Q_3}{4} \quad (42)$$

(x) Trimmed mean: A score calculated by discarding a certain percentage of the lowest and the highest scores and then computing the mean of the remaining scores. For example, a mean trimmed 50% is computed by discarding the lower and higher 25% of the scores and taking the mean of the remaining scores. For further example, the median is the mean trimmed 100% and the arithmetic mean is the mean trimmed 0%. The trimmed mean is generally less susceptible to the effects of extreme scores than is the arithmetic mean. It is therefore less susceptible to sampling fluctuation than the mean for skewed distributions. It is generally less efficient than the mean for normal distributions. By way of example, the mean trimmed 50% is described by the following relationship:

$$\text{TrimmedMean}_{50} = \frac{\sum_{i=Q_1}^{Q_3} i \times h(i)}{\sum_{i=Q_1}^{Q_3} h(i)} \quad (43)$$

(xi) Range: The difference between the largest and the smallest values. The range can be a useful measure of spread. However, it is sensitive to extreme scores since it is based on only two values. Due to this sensitivity, the range is generally not used as the only measure of spread, but can nonetheless be informative if used as a supplement to other measures of spread such as standard deviation or semi-interquartile range.

(xii) Semi-interquartile range: A measure of spread computed as one-half the difference between the 75th percentile (Q3) and the 25th percentile (Q1). Since half of the scores in a distribution lie between Q3 and Q1, the semi-interquartile range is half the distance needed to cover said half of the scores. In a symmetric distribution, an interval stretching from one semi-interquartile range below the median to one semi-interquartile above the median will contain half of the scores. This is not true for a skewed distribution, however. Unlike range, semi-interquartile range is generally not substantially affected by extreme scores. However, it is more subject to sampling fluctuation in normal distributions than is standard deviation, and therefore is not often used for approximately normally distributed data. Semi-interquartile range is defined according to the following relationship:

$$SemiInterQuartilRange = \frac{Q_3 - Q_1}{2} \quad (44)$$

(xiii) Variance: A measure of distribution spread. Variance is calculated by taking the average squared deviation of each number from its mean, according to the following relationship:

$$Variance = \frac{1}{n-1} \sum_{i=min}^{max} h(i) \times (i - Mean)^2 \quad (45)$$

(xiv) Standard deviation: A function of variance that measures how widely the values of a distribution are dispersed from the mean. Standard deviation is the square root of the variance. Although generally less sensitive to extreme scores than the range, standard deviation is generally more sensitive than semi-interquartile range. Thus, semi-interquartile range may be used to supplement standard deviation when the possibility of extreme scores exists.

(xv) Skewness: A measure of a distribution's asymmetry around its mean. A distribution is skewed if one of its tails is longer than the other. Positive skewness indicates a distribution with an asymmetric tail extending toward more positive values (greater than the mean). Negative skewness indicates a distribution with an asymmetric tail extending toward more negative values (less than the mean). Skewness may be calculated according to the following relationship:

$$Skew = \frac{N}{(N-1) \times (N-2)} \sum_{i=min}^{max} \left( h(i) \times \left( \frac{i - Mean}{StdDev} \right)^3 \right) \quad (46)$$

(xvi) Kurtosis: A measure of steepness or flatness of a distribution (or a relative peak width), as compared to a normal distribution. Positive kurtosis indicates a relatively peaked distribution. Negative kurtosis indicates a relatively flat distribution. Kurtosis is based on the size of a distribution's tails and is determined by the following relationship:

$$Kurtosis = \frac{N \times (N+1)}{(N-1) \times (N-2) \times (N-3)} \sum_{i=min}^{max} \left( h(i) \times \left( \frac{i - Mean}{StdDev} \right)^4 \right) - 3 \frac{(N-1)^2}{(N-2) \times (N-3)} \quad (47)$$

The above statistical methods are useful for analyzing spatial distributions of grey values, by computing local features at each point in the image, and deriving a set of statistics from the distributions of the local features. With these statistical methods, textures for the analyzed regions can be described and statically defined.

Texture can be characterized using texture descriptors. Texture descriptors can be computed over a given region of the image (discussed in greater detail below). One commonly applied texture method is the co-occurrence method, introduced by Haralick, R., et al. "Texture features for image classification," IEEE Transactions of System, Man and Cybernetics, Vol. 3, pp. 610-621 (1973), which is incorporated by reference herein. In this method, the relative frequencies of grey level pairs of pixels separated by a distance d in the direction θ are combined to form a relative displacement vector (d, θ). The relative displacement vector is computed and stored in a matrix, referred to as grey level co-occurrence matrix (GLCM). This matrix is used to extract second-order statistical texture features. Haralick suggests fourteen different features to describe a two dimensional probability density function pij, four of which features are more commonly used than the others:

Texture can be characterized using texture descriptors. Texture descriptors can be computed over a given region of the image (discussed in greater detail below). One commonly applied texture method is the co-occurrence method, introduced by Haralick, R., et al. "Texture features for image classification," IEEE Transactions of System, Man and Cybernetics, Vol. 3, pp. 610-621 (1973), which is incorporated by reference herein. In this method, the relative frequencies of grey level pairs of pixels separated by a distance d in the direction θ are combined to form a relative displacement vector (d, θ). The relative displacement vector is computed and stored in a matrix, referred to as grey level co-occurrence matrix (GLCM). This matrix is used to extract second-order statistical texture features. Haralick suggests fourteen different features to describe a two dimensional probability density function pij, four of which features are more commonly used than the others:

Angular Second Moment (ASM) is calculated by the following:

$$ASM = \sum_{i=0}^{N-1} \sum_{j=0}^{N-1} p_{i,j}^2 \quad (48)$$

(ii) Contrast (Con) is calculated by the following:

$$Con = \sum_{i=0}^{N-1} \sum_{j=0}^{N-1} (i-j)^2 p_{ij} \quad (49)$$

(iii) Correlation (Cor) is calculated by the following (in which $\sigma_x$ and $\sigma_y$ are standard deviations of the corresponding distributions):

$$Cor = \frac{1}{\sigma_x \sigma_y} \sum_{i=0}^{N-1} \sum_{j=0}^{N-1} p_{ij} \log(p_{ij}) \quad (50)$$

(iv) Entropy (Ent) is calculated by the following:

$$Ent = \sum_{i=0}^{N-1} \sum_{j=0}^{N-1} p_{ij} \log(p_{ij}) \quad (51)$$

These four features are also listed in Strand, J., et al. "Local frequency features for the texture classification," Pattern Recognition, Vol. 27, No. 10, pp 1397-1406 (1994) [Strand94], which is also incorporated by reference herein.

For a given image, the region of the image over which the above features are evaluated may be defined by a mask (e.g., a colony mask), or by a Voronoï region of influence extending beyond the mask.

Figure 14:
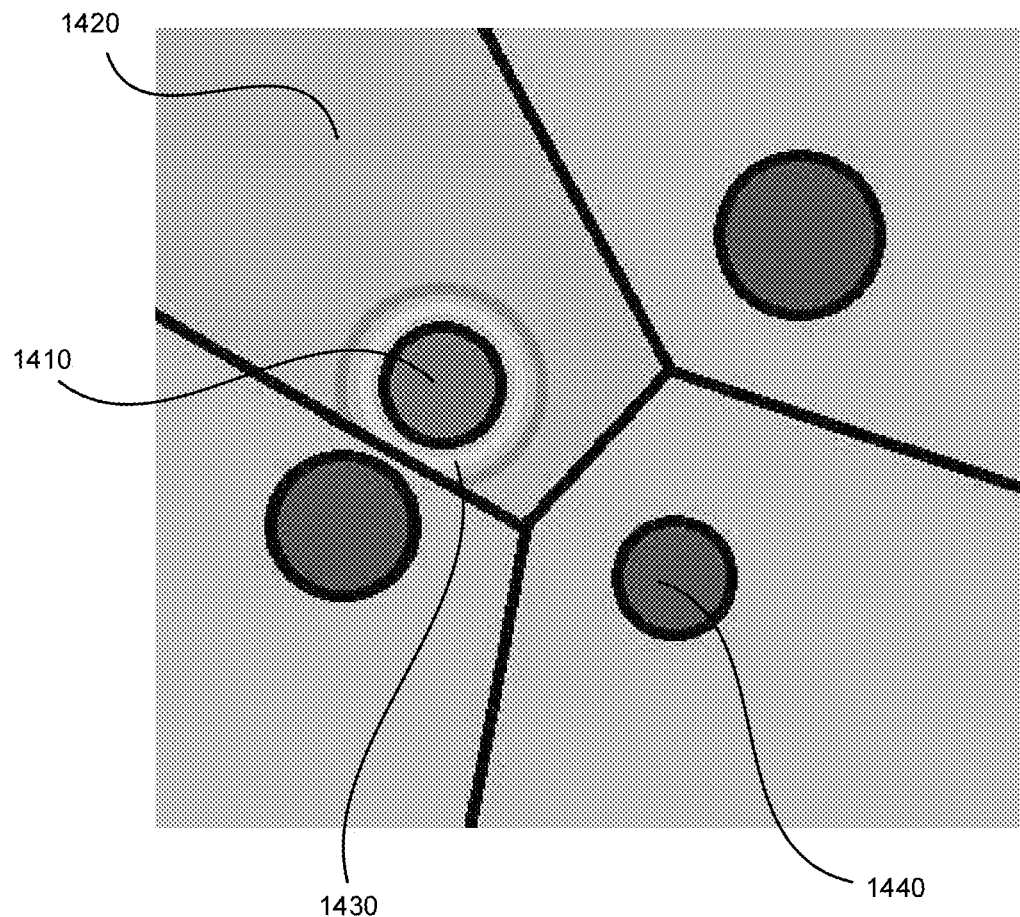
FIG. 14 is a diagram illustrating Voronoï regions of influence according to an aspect of the disclosure.

FIG. 14 illustrates a few possible regions. Region 1410 is a colony mask that extends only as far as the colony itself. Region 1420 is the Voronoï region of influence of the colony (bounded by the edge of the image or the plate). For further illustration, pixel 1430 is a pixel within region 1420 but outside of region 1410. In other words, the colony represented by region 1410 is expected to expand into pixel 1630 but has not done so yet. Pixel 1440 is a pixel outside of both regions 1410 and 1420. In other words, not only does the colony not occupy pixel 1410 at the time of the image, but it is not predicted to be occupied by the colony any time in the future either (in this case, it is already occupied by a different colony).

Using colony masks at the different time points along the incubation process and their associated Voronoï regions of influence as described above, it is possible to generate multiple histograms depicting different aspects of the colonies and their impact on local surrounding growing media. The colony masks and Voronoï regions of influence themselves may be adjusted over time, for instance as the colonies grow. For example, FIGS. 15A-C illustrate how growth of a colony can be used to adjust a mask of the colony over time. FIG. 15A is a portion of a blood culture after 24 hours of growth in agar. FIG. 15B is a contrast image of the same culture, as compared to an image previously captured at t0. FIG. 15C is a grey scale image illustrating growth at 9 hours (lightest), 12 hours (medium) and 24 hours (darkest). Each shade in FIG. 15C could be used to design a different mask for the colony. Alternatively or additionally, as growth occurs, the masks could be separated according to their respective Voronoï regions of influence.

Any one or combination of features in the above list of features may be used as a feature set for capturing specificities of organisms growing on various media of an imaged plate under various incubation conditions. This list is not meant to be exhaustive, and anyone knowledgeable in the field could modify, enlarge or restrict this feature set according to the intended objects to be imaged and the variety of image-processing-based features known in the field. Thus, the example features above are offered by way of illustration, not limitation.

Those skilled in the art are aware of other measurements and approaches to determine object shapes and features, and the examples above are offered by way of illustration, not limitation.

Contrast Building

It is often difficult to predict initially which image in an image series will bring values for growth detection, counting or identification. This is in part because image contrast varies for the different colony forming units (CFUs) and across different media. In a given image of several colonies, one colony may have highly desirable contrast with the background while another colony may not have adequate contrast with the background for growth detection. This also makes it difficult to use a single approach to identify colonies on media.

It is therefore desirable to build contrast from all available material through space (spatial differences) and time (temporal differences under common imaging conditions), as well as by using various imaging conditions (e.g., red, green and blue channels, light and dark backgrounds, spectral images or any other color space transformation). It is also desirable to gather contrast from multiple available sources to provide a standardized image as an input to an algorithm for detecting colonies.

Image data can be delimited based upon any number of factors. For example, image data can be limited to particular time points and/or particular information sought (e.g. spatial image information may not require as many time points as temporal image information requires). Illumination configurations and color spaces can also be selected to achieve specific contrast objectives. Spatial frequencies can also be varied in order to detect objects (e.g., colonies) having a desired size (or size within a target range).

To detect discrete objects, contrast can be set to absolute values on [0,1] or signed [−1,−1]. A scale and an offset of the contrast output can also be specified (e.g., for 8 bits image with signed contrast offset can be 127.5 and the scale can be 127.5). In an example where the contrast is set to an extreme, the absolute offset may set to zero and the scale to 256.

Spatial contrast may be used to detect discrete objects on a homogeneous background. A formula may be utilized to provide automated evaluation of spatial contrast $C_{(x,y)}^{I,r}$ on an image I at location (x, y) within distance r. In one embodiment, in which distance r is limited to distances greater than or equal to $\sqrt{(x_i-x)^2+(y_i-y)^2}$, and a contrast operator K is used to control contrast settings, the following equations are applied:

$$C_{(x,y)}^{I,r} = \frac{|I_{(x,y)} - K_{(x_i,y_i,r)}|}{I_{(x,y)} + K_{(x_i,y_i,r)}} \quad (52)$$

$$K_{(x_i,y_i,r)} = \frac{1}{\pi r^2} \sum_r I_{(x_i,y_i)} \quad (53)$$

Temporal contrast may be used to detect moving objects or objects changing over time (such as CFUs appearing and or expending on an imaged plate). A formula may be utilized to provide automated evaluation of temporal contrast $C_{(x,y)}^{I(T_x,T_0)}$ on an image I at location (x, y) between times t0 and tx. In one embodiment, the following equation is applied:

$$C_{(x,y)}^{I(t_x,t_0)} = \frac{|I_{(x,y)}^{t_x} - I_{(x,y)}^{t_0}|}{I_{(x,y)}^{t_x} + I_{(x,y)}^{t_0}} \quad (54)$$

Spatial contrast gathering can be implemented in an automated fashion by generating a plurality of SHQI images of a plate according to a pre-programmed sequence. Multiple images would be generated at a given incubation time $t_0$ further colony detection investigations. In one embodiment, in which image data (particularly, a vector "vect" used to provide contrast inputs to the contrast gathering operator) is collected over several configurations (CFG1 through CFGN) at several different radii from the detected colony (Rmin through Rmax) at a given time according to the following:

$$C_{(x,y)}^{(R_{min},R_{max})} = \underset{(R_{min},R_{max})}{\overset{vect\langle CFG_1,\ldots,CFG_N\rangle}{\text{Max}}} \left( \frac{|I_{(x,y)} - K_{(x_i,y_i,r)}|}{I_{(x,y)} + K_{(x_i,y_i,r)}} \right) \quad (55)$$

If SNR is known for a given image $I_{(x,y)}$ (e.g., when SHQI imaging is the source), the configuration in which SNR weighted contrast is maximized may be identified as the best configuration (Best CFG) when:

$$\underset{(R_{min},R_{max})}{CFG} \left( \frac{|I_{(x,y)} - K_{(x_i,y_i,r)}|}{I_{(x,y)} + K_{(x_i,y_i,r)}} \right) * SNR_{(x,y)} \text{ is maximum over:} \quad (56)$$

$$\underset{(R_{min},R_{max})}{vect\langle CFG_1,\ldots,CFG_N\rangle} \left( \frac{|I_{(x,y)} - K_{(x_i,y_i,r)}|}{I_{(x,y)} + K_{(x_i,y_i,r)}} \right) = SNR_{(x,y)} \quad (57)$$

The contrast operator K further benefits from this known SNR information and the above equation becomes:

$$C_{(x,y)}^{(R_{min},R_{max})} = \underset{(R_{min},R_{max})}{\overset{vect\langle CFG_1,\ldots,CFG_N\rangle \text{ Best } CFG}{}} \left( \frac{|I_{(x,y)} - K_{(x_i,y_i,r)}|}{I_{(x,y)} + K_{(x_i,y_i,r)}} \right) \quad (58)$$

Temporal contrast gathering can also be implemented in an automated fashion by generating a plurality of SHQI images of a plate according to a pre-programmed sequence. Multiple images would be generated over multiple incubation times, at least one of which is t0, to further colony detection investigations. In one embodiment, image data is collected over several configurations at time t0 and one or more subsequent incubation times up to time tx according to the following:

$$C_{(x,y)}^{vect\langle t_0,\ldots,t_x\rangle} = vect\langle CFG_1,\ldots,CFG_N\rangle \text{Max} \left( \frac{|I_{(x,y)}^{N t_x} - I_{(x,y)}^{t_0}|}{I_{(x,y)}^{N t_x} + I_{(x,y)}^{t_0}} \right) \quad (59)$$

In the above example, the vector may be a vector between two time points (e.g., t0 and tx) based upon differences in the images at those two times. However, in other applications, in which additional times between t0 and tx are included, the vector may be mapped over as many points as there are times at which images are taken. Mathematically speaking, there is no limit to the number points that may be included in vector.

As with spatial contrast, if SNR is known for a given image $I_{(x,y)}$, the configuration in which SNR weighted contrast is maximized may be identified as the best configuration (Best CFG) when:

$$CFG \left( \frac{|I_{(x,y)}^{N t_x} - I_{(x,y)}^{t_0}|}{I_{(x,y)}^{N t_x} + I_{(x,y)}^{t_0}} \right) * SNR_{(x,y)} \text{ is maximum over} \quad (60)$$

$$vect\langle CFG_1,\ldots,CFG_N\rangle \left( \frac{|I_{(x,y)}^{N t_x} - I_{(x,y)}^{t_0}|}{I_{(x,y)}^{N t_x} + I_{(x,y)}^{t_0}} \right) * SNR_{(x,y)} \quad (61)$$

The contrast operator K further benefits from this known SNR information and the above equation becomes:

$$C_{(x,y)}^{vect\langle t_0,\ldots,t_x\rangle} = vect\langle CFG_1,\ldots,CFG_N\rangle \text{ Best } CFG \left( \frac{|I_{(x,y)}^{N t_x} - I_{(x,y)}^{t_0}|}{I_{(x,y)}^{N t_x} + I_{(x,y)}^{t_0}} \right) \quad (62)$$

In the above examples, the Max operator could be replaced by any other statistical operator such as a percentile (e.g., Q1, median, Q3, or any other percentile) or weighted sum. Weighted values could originate from pre-work extracted from a training database, thereby opening the field of supervised contrast extraction to neural networks. Additionally, multiple algorithms may be used, with the results of the multiple algorithms being further combined using another operator, such as the Max operator.

Image Alignment

When multiple images are taken over time, very precise alignment of images is needed in order to obtain valid temporal estimations from them. Such alignment can be achieved by way of a mechanical alignment device and/or algorithms (e.g., image tracking, image matching). Those knowledgeable in the field are cognizant of these solutions and techniques to achieve this goal.

For instance, in cases where multiple images of an object on the plate are collected, the coordinates of an object's location may be determined. Image data of the object collected at a subsequent time may then be associated with the previous image data based on the coordinates, and then used to determine the change in the object over time.

Figure 16A:
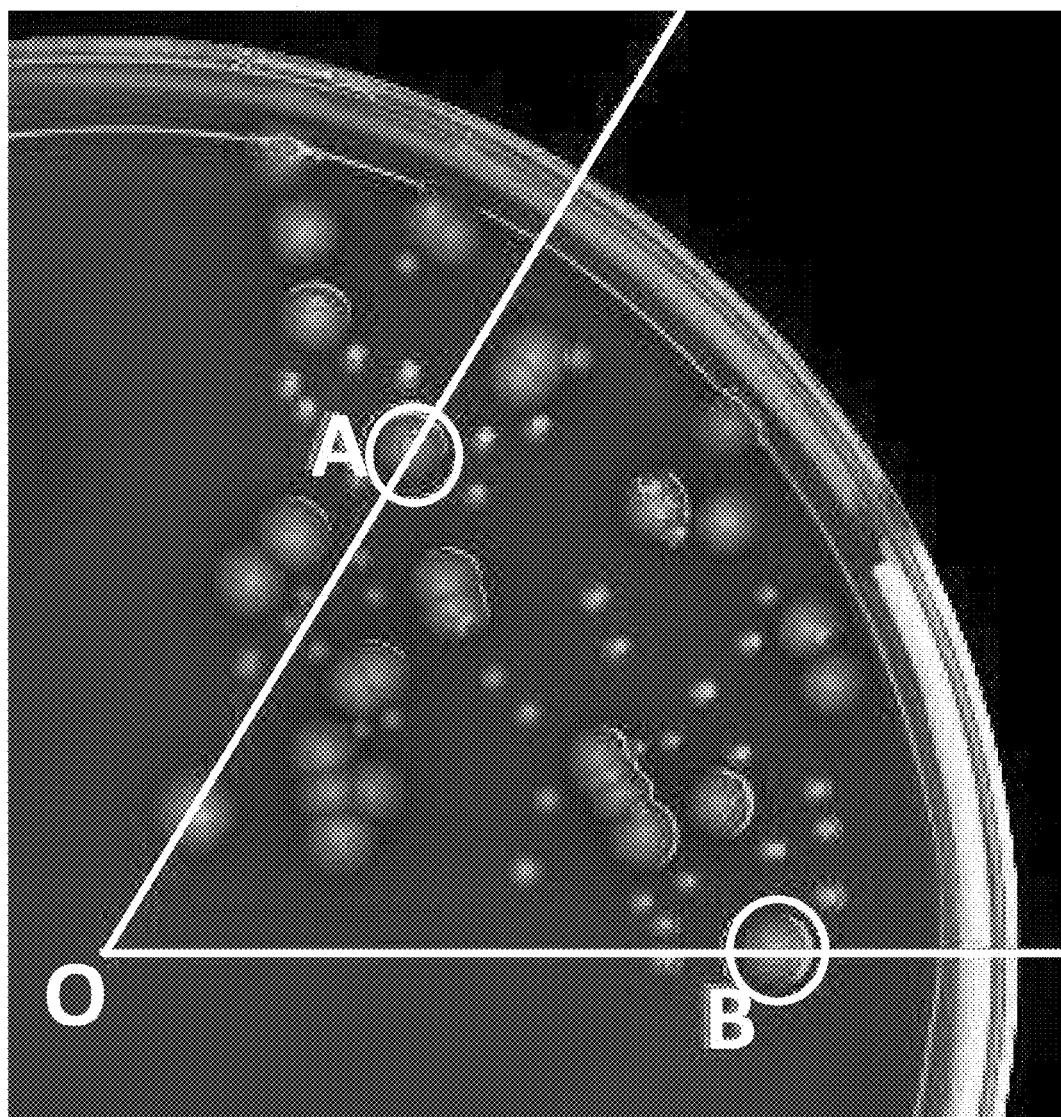
FIGS. 16A and 16B show a section of an imaged plate, with zoomed and reoriented images of sample colonies of the image.
Figure 16B:
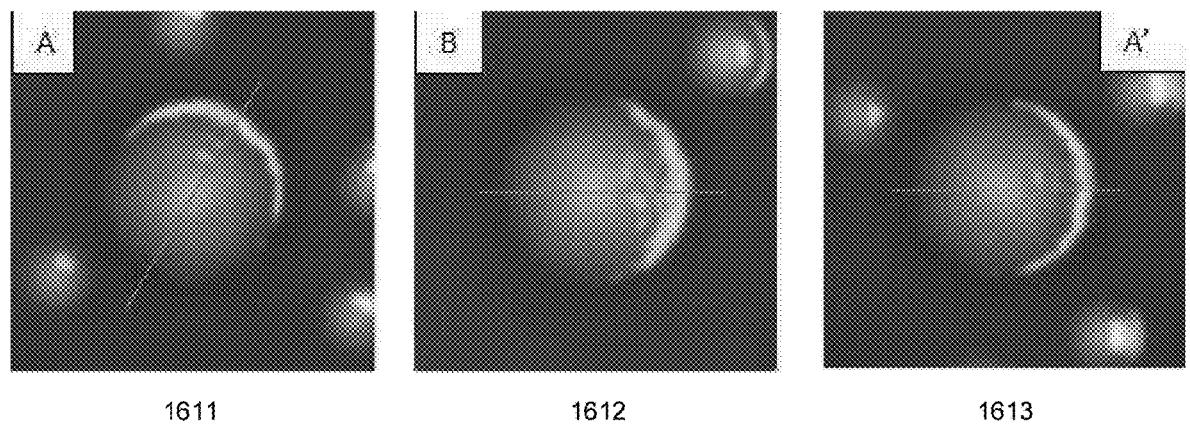

For rapid and valuable usage of images (e.g., when used as input to classifiers), it is important to store the images in a spatial reference to maximize their invariance. As the basic shape descriptor for a colony is generally circular, a polar coordinate system can be used to store colony images. The colony center of mass may be identified as the center of the location of the colony when the colony is first detected. That center point may later serve as origin center for a polar transform of each subsequent image of the colony. FIG. 16A shows a zoomed portion of an imaged plate having a center point "O." Two rays "A" and "B" extending from point "O" are shown (for purposes of clarity) overlaid on the image. Each ray intersects with a respective colony (circled). The circled colonies of FIG. 16A shown in even greater detail in the images 1611 and 1612 FIG. 16B. In FIG. 16B, image 1611 (the colony intersecting ray "A") is reoriented into image 1613 ("A'") such that the radial axis of image 1613 is aligned with that of image 1612, such that the leftmost part of the reoriented image is closest to point "O" of FIG. 16A, and the rightmost part of the reoriented image is farthest from point "O." This polar reorientation allows for easier analysis of the differently oriented (with respect to such factors as illumination) colonies of an imaged plate.

Figure 16C:
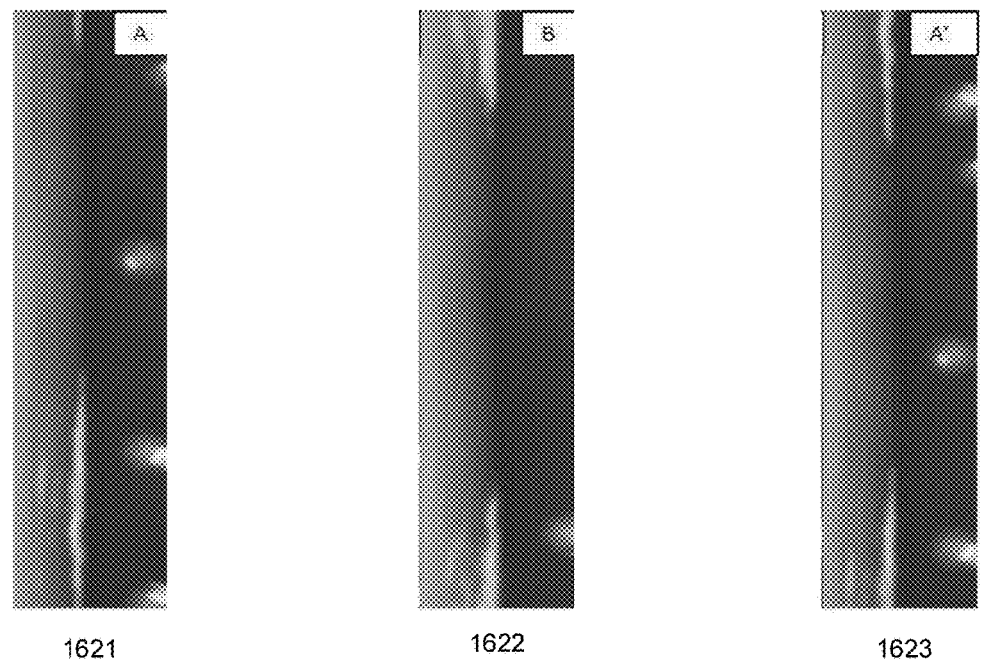
FIG. 16C shows vector diagrams of the respective images of FIG. 16B.

In FIG. 16C, a polar transform is completed for each of the images 1611, 1612 and 1613 of FIG. 16B. In the polar transform images 1621, 1622 and 1623, the radial axis of the respective reoriented images 1611, 1612 and 1613 (extending from the center of each respective imaged colony) are plotted from left to right in the images of FIG. 16C, and the angular axis (of the respective colonies) is plotted from top to bottom.

For each polar image, summary one-dimensional vector sets can be generated using, for example, shape features and/or histogram features (e.g., average and/or standard deviation of color or intensity of an object) along the radial and/or angular axis. Even if shape and histogram features are mostly invariant when considering rotation, it is possible that some texture features will show significant variations when rotated; thus, invariance is not guaranteed. Therefore, there is a significant benefit to presenting each of the colony images from the same viewpoint or angle illumination-wise, as the objects' texture differences can then be used to discriminate among each other. As illumination conditions mostly show variations linked to angular position around a plate imaging center, the ray going through the colony and plate center (shown as a line in each of images 1611, 1612 and 1613 of FIG. 16B) may serve as origin (θ) for each image polar transform.

A further alignment challenge arises from the fact that the plate media is not absolutely frozen and rigid, and therefore may slightly shift from one taken to the next. Therefore, one cannot absolutely assume that the region of a plate at certain coordinates of an image taken at one time will necessarily perfectly align with the region of the plate at the same coordinates taken at a later time. Stated another way, slight deformations of the media may lead to a little uncertainty regarding the exact matching of a given pixel with the corresponding pixel captured at a different time point during the incubation process.

In order to account for this uncertainty, a given pixel intensity value at time ta, $I_{(x,y)}^{ta}$, can be compared with the closest intensity value in the local neighborhood N(x, y) of this pixel at a different time point tb, $I_{N(x,y)}^{tb}$. Selection of a local neighborhood may involve determining one or more errors or inaccuracies in the repositioning of the imaged plate from one time to the next (e.g., a position accuracy error due to imperfect repositioning of the imaged media, a parallax error due to an unknown height of the imaged media from one time to the next). In one example, it has been observed that setting "x" and "y" within the range of about 3 to about 7 pixels is suitable for an image with resolution of about 50 microns per pixel.

Anyone knowledgeable in the field will recognize as an efficient solution to generate two tb images from the tb source image: the first corresponding to a grey level dilation of tb (referred to as $DIL^{tb,d}$), and the second to a grey level erosion of tb, (referred to as $ERO^{tb,d}$), both with a kernel size matching the repositioning distance uncertainty d.

If $ERO_{(x,y)}^{tb,d} \le I_{(x,y)}^{ta} \le DIL_{(x,y)}^{tb,d}$ then the contrast is 0, otherwise the contrast is estimated from the closest value to $I_{(x,y)}^{Ta}$ among $ERO_{(x,y)}^{tb,d}$ and $DIL_{(x,y)}^{tb,d}$ using the following:

$$C_{(x,y)}^{(ta,tb)} = \left( \frac{|I_{(x,y)}^{ta} - K_{(x,y)}^{tb}|}{I_{(x,y)}^{ta} + K_{(x,y)}^{tb}} \right) \quad (63)$$

$$K_{(x,y)}^{tb} = ERO_{(x,y)}^{tb,d} \left( |ERO_{(x,y)}^{tb,d} - I_{(x,y)}^{ta}| < |DIL_{(x,y)}^{tb,d} - I_{(x,y)}^{ta}| \right) \quad (64)$$

$$K_{(x,y)}^{tb} = DIL_{(x,y)}^{tb,d} \left( |DIL_{(x,y)}^{tb,d} - I_{(x,y)}^{ta}| \le |ERO_{(x,y)}^{tb,d} - I_{(x,y)}^{ta}| \right) \quad (65)$$

Improvement Of SNR

Under typical illumination conditions, the photon shot noise (statistical variation in the arrival rate of incident photons on the sensor) limits the SNR of the detection system. Modern sensors have a full well capacity that is about 1,700 to about 1,900 electrons per active square micron. Thus, when imaging an object on a plate, the primary concern is not the number of pixels used to image the object but rather the area covered by the object in the sensor space. Increasing the area of the sensor improves the SNR for the imaged object.

Image quality may be improved by capturing the image with illumination conditions under which photon noise governs the SNR (photon noise=√signal) without saturating the sensor (maximum number of photons that can be recorded per pixel per frame). In order to maximize the SNR, image averaging techniques are commonly used. These techniques are used to address images with significant brightness (or color) differences since the SNR of dark regions is much lower than the SNE of bright regions, as shown by the following formula:

$$\left( SNR_{dark} = \frac{SNR_{bright}}{\sqrt{\frac{I_{bright}}{I_{dark}}}} \right). \quad (66)$$

In which I is the average current created by the electron stream at the sensor. As colors are perceived due to a difference in absorption/reflection of matter and light across the electromagnetic spectrum, confidence on captured colors will depend upon the system's ability to record intensity with a high SNR. Image sensors (e.g. CCD sensors, CMOS sensors, etc.) are well known to one skilled in the art and are not described in detail herein.

To overcome classical SNR imaging limitations, the imaging system may conduct analysis of an imaged plate during the image acquisition and adjust the illumination conditions and exposure times in real time based on the analysis. This process is described in PCT Publication No. WO2015/114121, incorporated by reference, and generally referred to as Supervised High Quality Imaging (SHQI). The system can also customize the imaging conditions for the various brightness regions of the plate within the different color channels.

For a given pixel x,y of an image, SNR information of the pixel acquired during a current frame N may be combined with SNR information of the same pixel acquired during previous or subsequent acquired frames (e.g., N−1, N+1). By example, the combined SNR is dictated by the following formula:

$$SNR_{x,y,N+1}' = \sqrt{SNR_{x,y,N}'^2 + SNR_{x,y,N+1}^2} \quad (67)$$

After updating the image data with a new acquisition, the acquisition system is able to predict the best next acquisition time that would maximize SNR according to environmental constraints (e.g. minimum required SNR per pixel within a region of interest). For example, averaging 5 images captured in non-saturating conditions will boost the SNR of a dark region (10% of max intensity) by √5, when merging the information of two images captured in bright and dark conditions optimum illumination will boost the dark regions SNR by √11 in only two acquisitions.

Image Modelling

In some circumstances, when calculating spatial or temporal contrast between pixels of one or more images, the pixel information for a given image may not be available, or may be degraded. Unavailability may occur, for instance, if an image of the plate was not captured within the time before bacterial growth (e.g., the plate was not imaged at time t0 or shortly thereafter. Degradation of signal information may occur, for instance, when an image is captured at time t0, but pixels of the captured image do not accurately reflect the imaged plate prior to bacterial growth. Such inaccuracies may be caused by temporary artifacts that do not reappear in subsequent time-series images of the plate (e.g., condensation temporarily forming underneath the plate due to thermal shock when the plate is first put into the incubator).

In such circumstances, the unavailable or degraded image (or certain pixels of the image) may be replaced or enhanced with a model image of a plate. The model image may provide pixel information reflecting how the plate is expected to look at the particular time of the unavailable or degraded image. In the case of a model image at time t0, the model may be a plain or standard image of a plate, and may be mathematically constructed using three-dimensional imaging/modelling techniques. The model may include each of physical design parameters (e.g., diameter, height, dividers for housing multiple media, plastic material, etc.), media parameters (e.g., type of media, media composition, media height or thickness, etc.) illumination parameters (e.g., angle of light source, color or wavelength(s) of light source, color of background, etc.) and positioning parameters (e.g., position of plate in imaging chamber) in order to produce as real a model as possible.

In the case of a degraded image, enhancement of the degraded image may be accomplished using signal restoration to sharpen the degraded pixel characteristics of the image when the pixel information is not as sharp as the rest of the image (e.g., due to condensation underneath blocking some light from passing through the plate and therefore making the section of the plate with condensation slightly less transparent). Signal restoration may involve determining intensity information for the rest of the image, identifying a median intensity of the intensity information, and then replacing the intensity information for the less sharp regions of the image with the median intensity of the rest of the image.

Applications

The present disclosure is based largely on testing performed in saline at various dilutions to simulate typical urine reporting amounts (CFU/ml Bucket groups). A suspension for each isolate was adjusted to a 0.5 McFarland Standard and used to prepare dilutions at estimated $1 \times 10^6$, $1 \times 10^5$, $5 \times 10^4$, $1 \times 10^4$, $1 \times 10^3$, and $1 \times 10^2$ CFU/ml suspension in BD Urine Vacutainer tubes (Cat. No. 364951). Specimen tubes were processed using Kiestra InoqulA (WCA1) with the standard urine streak pattern—#4 Zigzag (0.01 ml dispense per plate).

Plates were processed using the ReadA Compact (35 oC, non CO2) and imaged every 2 hours for the first 24 hours and every 6 hours for the second 24 hours with a total incubation of 48 hours. Incubation times were entered as first reading at 1 hour with allowed margin set as +/−15 minutes. For the next reading at 2-24 hours were set for every two hours with an allowed margin of +/−30 minutes. For reading 24-48 were set for every 6 hours with allowed margins of +/−30 minutes. After the pure feasibility studies, this was changed to eliminate the allowed margin. This was done to improve image acquisitions at the desired 18 to 24 hour time range.

In other cases, images could be obtained over a span of 48 hours, at two hour intervals for the first 24 hours and then at 6 hour intervals for the next 24 hours. In such cases, a total of seventeen images would be obtained in the 48 hour span, including an image obtained from time t0 (0 hours).

All acquired images were corrected for lens geometrical and chromatic aberrations, spectrally balanced, with known object pixel size, normalized illumination conditions and high signal to noise ratio per band per pixel. Suitable cameras for use in the methods and systems described herein are well known to one skilled in the art and not described in detail herein. As an example, using a 4-megapixel camera to capture a 90 mm plate image should allow enumeration up to 30 colonies/mm2 local densities (>105 CFU/plate) when colonies are in the range of 100 μm in diameter with adequate contrast.

The following media were used evaluate the contrast of colonies grown thereon:

TSAII 5% Sheep blood (BAP): a non selection media with worldwide usage for urine culture.

BAP: used for colony enumeration and presumptive ID based on colony morphology and hemolysis.

MacConkey II Agar (MAC): a selective media for most common Gram negative UTI pathogens. MAC is used for differentiation of lactose producing colonies. MAC also inhibits Proteus swarming. BAP and MAC are commonly used worldwide for urine culture. Some media are not recommended for use for colony counting due to partial inhibition of some gram negatives.

Colistin Nalidixic Acid agar (CNA): a selective media for most common Gram positive UTI pathogens. CNA is not as commonly used as MAC for urine culture but helps to identify colonies if over-growth of Gram negative colonies occurs.

CHROMAgar Orientation (CHROMA): a non-selection media used worldwide for urine culture. CHROMA is used for colony enumeration and ID based on colony color and morphology. *E. coli* and *Enterococcus* are identified by the media and do not require confirmatory testing. CHROMA is used less than BAP due to cost. For mixed samples, CLED media was also used.

Cystine Lactose Electrolyte-Deficient (CLED) Agar: used for colony enumeration and presumptive ID of urinary pathogens based on lactose fermentation.

The Specimen Processing BD Kiestra™ InoqulA™ was used to automate the processing of bacteriology specimens to enable standardization and ensure consistent and high quality streaking. The BD Kiestra™ InoqulA™ specimen processor uses a magnetic rolling bead technology to streak media plates using customizable patterns. The magnetic rolling bead is 5 mm in diameter.

Figure 17:
FIG. 17 depicts SHQI, spatial contrast, and temporal contrast images of a specimen according to an aspect of the disclosure.

FIG. 17 illustrates one example of contrast gathering algorithm performance in retrieving *Morganella morganii* growth on both CHROMagar (top images) and blood agar (bottom images) media. CHROMagar and BAP are both non-selective growing media commonly used in microbiology laboratories. Each of the middle images of FIG. 17 presents an imaged plate illuminated from a light above the plate (top illumination). The images on the left present corresponding spatial contrast of the middle images. The spatial contrast is based on a 1 millimeter median kernel. Lastly, the images on the right present temporal contrast of the middle image. The temporal contrast is compiled from images captured between 0 hours (t0) and 12 hours (tx) of incubation using various lighting conditions (different color channels, illumination settings, etc.) at each image capture time.

As shown in FIG. 17, local contrast has its limitations when dealing with semitransparent colonies, especially where edge transitions are small, as only the most contrasted confluence regions can be picked out from the image using the spatial contrast algorithm alone. the spatial contrast can fail to pick up the object. Also evident from FIG. 17 is the efficiency of temporal contrast on isolated colonies.

FIG. 17 (particularly the blood agar images on the bottom) also highlights the issues of using spatial contrast alone to detect growth on transparent media. The ink printed on the transparent case has very strong edges, and thus strong spatial contrast. This ends up making any other spatial contrast very difficult to see, since the colonies do not have as strongly defined edges. Thus, the use of temporal contrast in conjunction with spatial contrast is of considerable benefit in the present disclosure.

Ultimately, the result of the above described contrast determinations is that methods for rapid detection and identification of colonies in an imaged media can be automated. The automated methods provide significant advantages over comparable manual methods.

Figure 18:
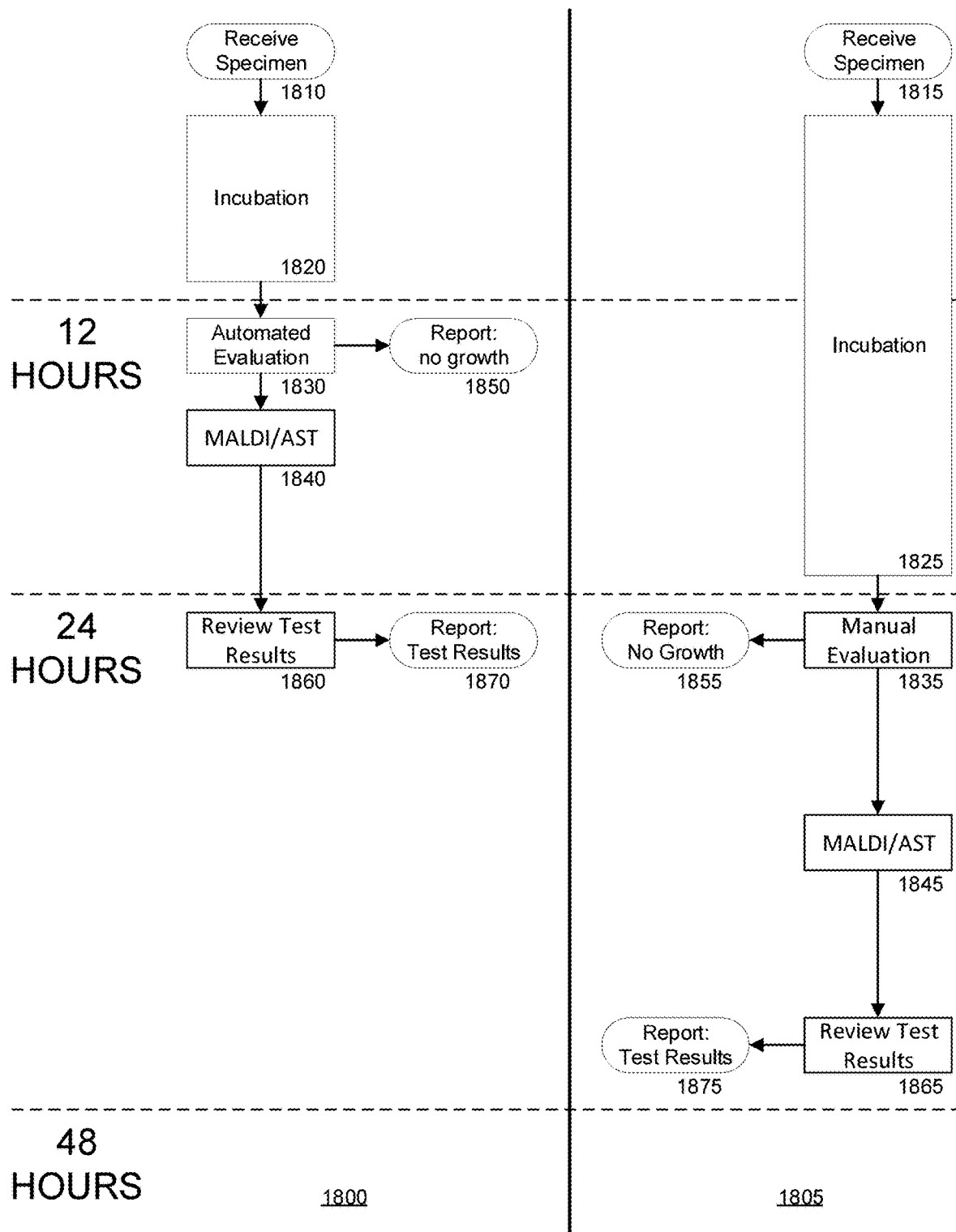
FIG. 18 is a flow chart comparing the timeline of the routine of FIG. 2 to the timeline of a comparable manually-performed routine.

FIG. 18 shows a pair of flow charts comparing a timeline of an automated test process 1800 (e.g., the routine 200 of FIG. 2) to a timeline of a comparable manually-performed test process 1805. Each process begins with the specimen for testing being received at a laboratory 1810, 1815. Each process then proceeds with incubation 1820, 1825, during which the specimen may be imaged several time. In the automated process, an automated evaluation 1830 is made after approximately 12 hours of incubation, after which time it can be definitively determined whether there is no growth (or normal growth) in the specimen 1840. As shown from the results in FIG. 17, the use of temporal contrast in the automated process greatly improves the ability to detect colonies, even after only 12 hours. By contrast, in the manual process, a manual evaluation 1835 cannot be made until nearly 24 hours into the incubation process. Only after 24 hours can it be definitively determined whether there is no growth (or normal growth) in the specimen 1845.

The use of an automated process also allows for faster AST and MALDI testing. Such testing 1850 in an automated process can begin soon after the initial evaluation 1830, and the results can be obtained 1860 and reported 1875 by the 24 hour mark. By contrast, such testing 1855 in a manual process often does not begin until close to the 36 hour mark, and takes an additional 8 to 12 hours to complete before the data can be reviewed 1865 and reported 1875.

Altogether, the manual test process 1805 is shown to take up to 48 hours, requires a 18-24 hour incubation period, only after which is the plate evaluated for growth, and further has no way to keep track of how long a sample has been in incubation. By contrast, because the automated test process 1800 can detect even relatively poor contrast between colonies (compared to background and each other), and can conduct imaging and incubation without a microbiologist having to keep track of timing, only 12-18 hours of incubation is necessary before the specimen can be identified and prepared for further testing (e.g., AST, MALDI), and the entire process can be completed within about 24 hours. Thus, the automated process of the present disclosure, aided with the contrast processing described herein, provides faster testing of samples without adversely affecting the quality or accuracy of the test results.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for evaluating microbial growth on plated media that has been inoculated with a culture and incubated, the method comprising:
    obtaining first and second digital images of the plated media, each digital image obtained after a period of incubation for the inoculated media and at a different time;
    identifying one or more static features in the first and second digital images;
    aligning the second digital image with the first digital image, wherein said alignment is based on coordinates assigned to pixels of the first digital image and one or more pixels of the second digital image corresponding to the pixels of the first digital image that were assigned to coordinates;
    generating temporal contrast data indicative of changes between corresponding pixels of the first and second digital images;
    identifying an object in the second digital image from the temporal contrast data;
    using a classifier to classify the identified object as a type of organism based on one or more dynamic object features of the identified object; and
    storing the identified object and its classification in memory.

2. The method of claim 1, wherein the one or more static features includes at least one of:
    polar coordinates of the object;
    a vector of the polar coordinates;
    morphometric features;
    contextual features;
    spectral features; or
    background features.

3. The method of claim 1, further comprising:
    obtaining a third digital image of the plated media after the period of incubation for the inoculated media and at a different time than when the first and second digital images were obtained;
    aligning the third digital image with the first and second digital images; and
    generating another temporal contrast data indicative of changes between corresponding pixels of the second and third digital images, wherein the object is identified based further on the another temporal contrast data, and wherein the one or more dynamic object features of the identified object includes a second derivative of the another temporal contrast data.

4. The method of claim 1, wherein the one or more dynamic object features of the identified object includes an object growth acceleration rate.

5. The method of claim 1, wherein the one or more dynamic object features of the identified object includes at least one of:
    a growth rate of the identified object;
    a change to a chromatic feature of the identified object; or
    a change in growth along an axis proximately normal to the plated media.

* * * * *